United States Patent
McNaughton et al.

(10) Patent No.: US 10,927,157 B2
(45) Date of Patent: *Feb. 23, 2021

(54) HELIX-GRAFTED PROTEINS AS INHIBITORS OF DISEASE-RELEVANT PROTEIN-PROTEIN INTERACTIONS

(71) Applicant: Colorado State University Research Foundation, Fort Collins, CO (US)

(72) Inventors: Brian R. McNaughton, Fort Collins, CO (US); Susanne N. Walker, Fort Collins, CO (US); Rachel L. Tennyson, Fort Collins, CO (US); Alan J. Kennan, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/534,171

(22) Filed: Aug. 7, 2019

(65) Prior Publication Data
US 2019/0352357 A1 Nov. 21, 2019

Related U.S. Application Data

(62) Division of application No. 14/936,200, filed on Nov. 9, 2015, now Pat. No. 10,428,128.

(60) Provisional application No. 62/076,959, filed on Nov. 7, 2014.

(51) Int. Cl.
*A61K 38/00* (2006.01)
*C07K 14/47* (2006.01)
*C07K 14/005* (2006.01)

(52) U.S. Cl.
CPC ........ *C07K 14/4722* (2013.01); *C07K 14/005* (2013.01); *A61K 38/00* (2013.01); *C07K 2319/33* (2013.01); *C12N 2740/16033* (2013.01); *C12N 2740/16122* (2013.01)

(58) Field of Classification Search
None
See application file for complete search history.

(56) References Cited

U.S. PATENT DOCUMENTS

| 10,428,128 B2 * | 10/2019 | McNaughton | ..... C07K 14/4722 |
| 2003/0219451 A1 * | 11/2003 | Sia | ..... C07K 14/765 424/188.1 |

OTHER PUBLICATIONS

Blast Search (Query = DKWEYWIWTIGLYTLLGK); retrieved from https://blast.ncbi.nlm.nih.gov/Blast.cgi on Jul. 10, 2017, 9 pages.
Chan DC, Fass D, Berger JM, Kim PS. Core Structure of gp41 from the HIV Envelope Glycoprotein. Cell. 1997;89:263-273.
Corrêa RO, Telles AS, Ourique JE. A Graph-Structural Method for Prediction of Polymer Properties. Brazilian Journal of Chemical Engineering. 2004;21(4):621-628.
Hanawa-Suetsugu et al. Supporting Information 10.1073/PNAS. 1113512109 (retrieved from http://www.pnas.org/content/pnas/suppl/2012/02/13/1113512109.DCSupplemental/pnas.1113512109_SI.pdf on Apr. 24, 2018, 9 pages, 2018.
Hanawa-Suetsugu K et al. Structural basis for mutual relief of the Rac guanine nucleotide exchange factor DOCK2 and its partner ELMOI from their autoinhibited forms. PNAS. 2012;109(9):3305-3310.
Komander D et al. An α-Helical Extension of the ELMO1 Pleckstrin Homology Domain Mediates Direct Interaction to DOCK180 and Is Critical in Rac Signaling Molecular Biology of the Cell. 2008;19;4837-4851.
Shiraishi-Yamaguchi Y, Furuichi T. The Homer family proteins. Biology. 2007;8:206.
Walker SN, Tennyson RL, Chapman AM, Kennan AJ, McNaughton BR. GLUE That Sticks to HIV: A Helix-Grafted GLUE Protein That Selectively Binds the HIV gp41 N-Terminal Helical Region. ChemBioChem. 2015;16:219-222.

* cited by examiner

*Primary Examiner* — Ronald T Niebauer
(74) *Attorney, Agent, or Firm* — Polsinelli PC

(57) ABSTRACT

The disclosure provides helix grafted proteins, methods of producing helix grafted proteins and methods of use of helix grafted proteins as inhibitors of protein-protein interactions involved in disease pathogenesis.

10 Claims, 18 Drawing Sheets
(14 of 18 Drawing Sheet(s) Filed in Color)
Specification includes a Sequence Listing.

expected mass (GLUE-Cpep) = 27,694 Da [M+1]
observed mass = 27,694 Da expected mass (GLUE-Cpep) = 27,920 Da [M+1]
observed mass = 27,920 Da

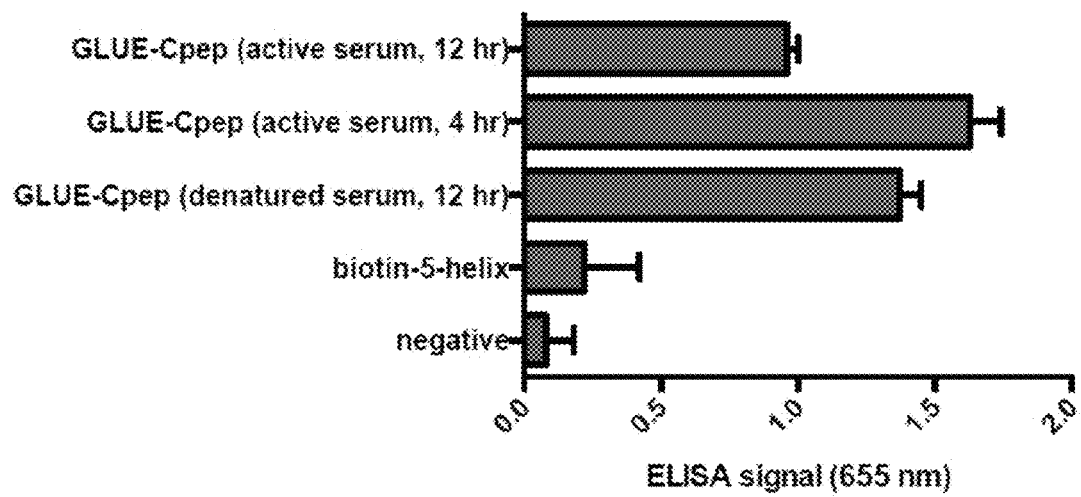
FIG. 8
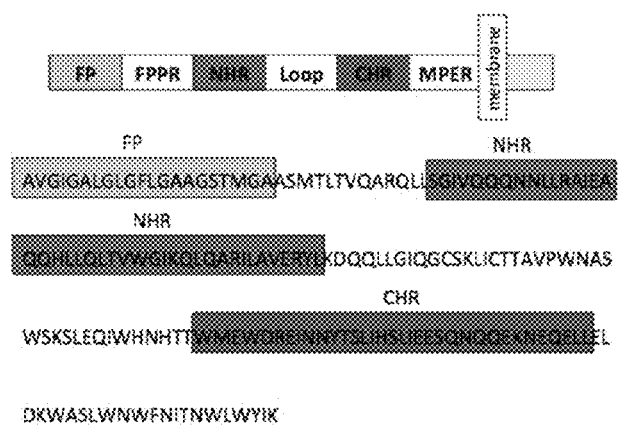 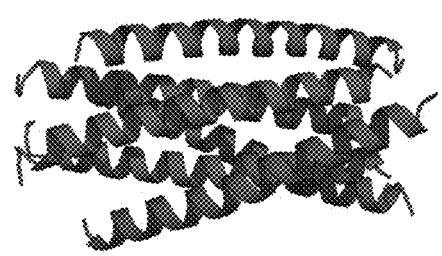
FIG. 9A                    FIG. 9B

1: wtGLUE      4: wtELMO
2: wtHOMER     5: wtAPPL1 PTB
3: wtPLECKSTRIN 6: wtAPPL1 PH

1: wtAKT2    3: wtDOK5
2: wtPKB     4: wtDynamin

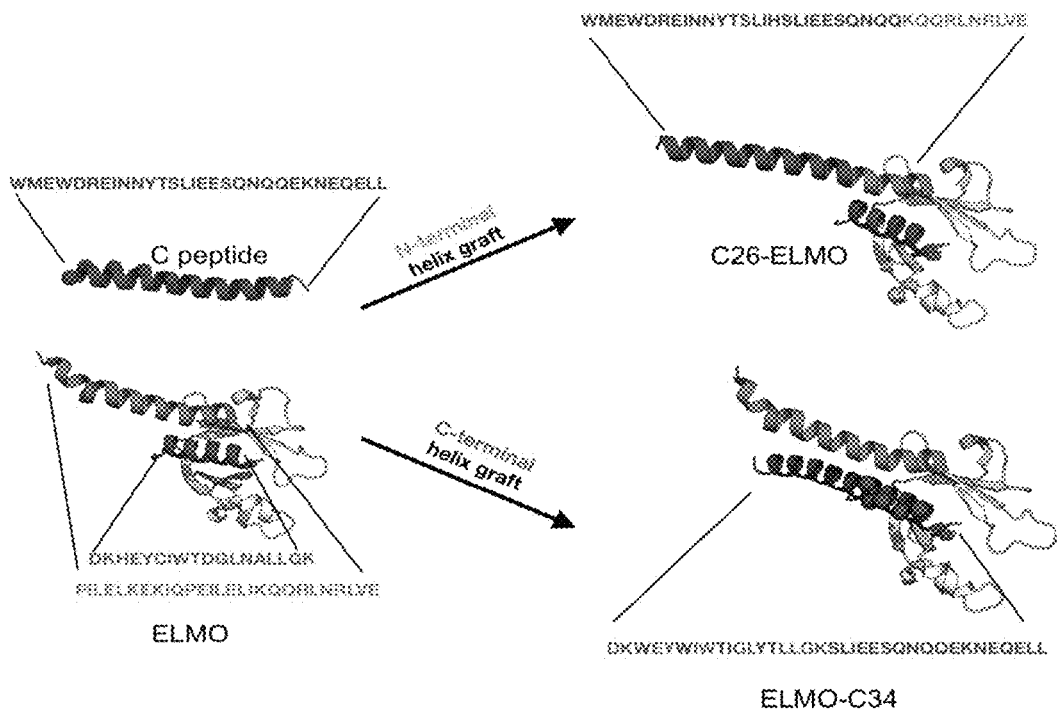
FIG. 13
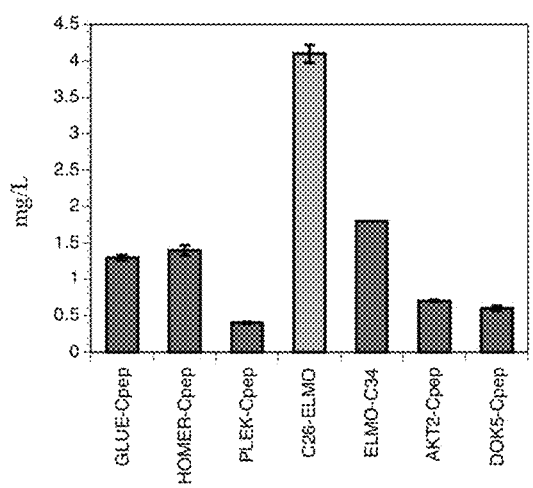
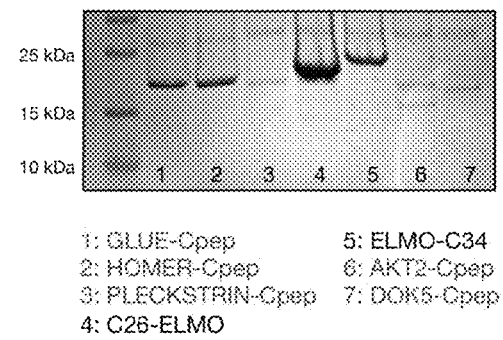
FIG. 14A  FIG. 14B

1. Avitag 5-Helix-His6x
2. 5-Helix-His6x / ELMO
3. 5-Helix-His6x / C26 ELMO
4. 5-Helix-His6x / ELMO C34

SEQUENCE LISTING

```
<160> NUMBER OF SEQ ID NOS: 19

<210> SEQ ID NO 1
<211> LENGTH: 17
<212> TYPE: PRT
<213> ORGANISM: Saccharomyces cerevisiae

<400> SEQUENCE: 1

Gly Val Leu Phe Ser Gln Ala Thr Glu Arg Ala Leu Glu Asn Ile Leu
1               5                   10                  15

Thr

<210> SEQ ID NO 2
<211> LENGTH: 34
<212> TYPE: PRT
<213> ORGANISM: Human immunodeficiency virus

<400> SEQUENCE: 2

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 3
<211> LENGTH: 36
<212> TYPE: PRT
<213> ORGANISM: Artificial Sequence
<220> FEATURE:
<223> OTHER INFORMATION: Synthetic

<400> SEQUENCE: 3

Gly Val Trp Phe Ser Trp Ala Thr Glu Ile Ala Leu Tyr Thr Ile Leu
1               5                   10                  15

Ile His Ser Leu Ile Glu Glu Ser Gln Asn Gln Gln Glu Lys Asn Glu
            20                  25                  30
```

```
Gln Glu Leu Leu
        35

<210> SEQ ID NO 4
<211> LENGTH: 171
<212> TYPE: PRT
<213> ORGANISM: Artificial Sequence
<220> FEATURE:
<223> OTHER INFORMATION: Synthetic

<400> SEQUENCE: 4

Ala Val Gly Ile Gly Ala Leu Gly Leu Gly Phe Leu Gly Ala Ala Gly
1               5                   10                  15

Ser Thr Met Gly Ala Ala Ser Met Thr Leu Thr Val Gln Ala Arg Gln
            20                  25                  30

Leu Leu Ser Gly Ile Val Gln Gln Gln Asn Asn Leu Leu Arg Ala Ile
        35                  40                  45

Glu Ala Gln Gln His Leu Leu Gln Leu Thr Val Trp Gly Ile Lys Gln
    50                  55                  60

Leu Gln Ala Arg Ile Leu Ala Val Glu Arg Tyr Leu Lys Asp Gln Gln
65                  70                  75                  80

Leu Leu Gly Ile Gln Gly Cys Ser Lys Leu Ile Cys Thr Thr Ala Val
                85                  90                  95

Pro Trp Asn Ala Ser Trp Ser Lys Ser Leu Glu Gln Ile Trp His Asn
            100                 105                 110

His Thr Thr Trp Met Glu Trp Asp Arg Glu Ile Asn Asn Tyr Thr Ser
        115                 120                 125

Leu Ile His Ser Leu Ile Glu Glu Ser Gln Asn Gln Gln Glu Lys Asn
    130                 135                 140

Glu Gln Glu Leu Leu Glu Leu Asp Lys Trp Ala Ser Leu Trp Asn Trp
145                 150                 155                 160

Phe Asn Ile Thr Asn Trp Leu Trp Tyr Ile Lys
                165                 170

<210> SEQ ID NO 5
<211> LENGTH: 27
<212> TYPE: PRT
<213> ORGANISM: Homo sapiens

<400> SEQUENCE: 5

Pro Ile Leu Glu Leu Lys Glu Lys Ile Gln Pro Glu Ile Leu Glu Leu
1               5                   10                  15

Ile Lys Gln Gln Arg Leu Asn Arg Leu Val Glu
            20                  25

<210> SEQ ID NO 6
<211> LENGTH: 18
<212> TYPE: PRT
<213> ORGANISM: Homo sapiens

<400> SEQUENCE: 6

Asp Lys His Glu Tyr Cys Ile Trp Thr Asp Gly Leu Asn Ala Leu Leu
1               5                   10                  15

Gly Lys

<210> SEQ ID NO 7
<211> LENGTH: 36
<212> TYPE: PRT
<213> ORGANISM: Artificial Sequence
```

<220> FEATURE:
<223> OTHER INFORMATION: Synthetic

<400> SEQUENCE: 7

Trp Met Glu Trp Asp Arg Glu Ile Asn Asn Tyr Thr Ser Leu Ile His
1               5                   10                  15

Ser Leu Ile Glu Glu Ser Gln Asn Gln Gln Lys Gln Gln Arg Leu Asn
            20                  25                  30

Arg Leu Val Glu
        35

<210> SEQ ID NO 8
<211> LENGTH: 36
<212> TYPE: PRT
<213> ORGANISM: Artificial Sequence
<220> FEATURE:
<223> OTHER INFORMATION: Synthetic

<400> SEQUENCE: 8

Asp Lys Trp Glu Tyr Trp Ile Trp Thr Ile Gly Leu Tyr Thr Leu Leu
1               5                   10                  15

Gly Lys Ser Leu Ile Glu Glu Ser Gln Asn Gln Gln Glu Lys Asn Glu
            20                  25                  30

Gln Glu Leu Leu
        35

<210> SEQ ID NO 9
<211> LENGTH: 142
<212> TYPE: PRT
<213> ORGANISM: Artificial Sequence
<220> FEATURE:
<223> OTHER INFORMATION: Synthetic

<400> SEQUENCE: 9

Met Gly Ser Ser His His His His His His Ser Gln Asp Pro Glu Tyr
1               5                   10                  15

Trp His Tyr Val Glu Thr Thr Ser Ser Gly Gln Pro Leu Leu Arg Glu
            20                  25                  30

Gly Glu Lys Asp Ile Phe Ile Asp Gln Ser Val Gly Leu Tyr His Gly
        35                  40                  45

Lys Ser Lys Ile Leu Gln Arg Gln Arg Gly Arg Ile Phe Leu Thr Ser
    50                  55                  60

Gln Arg Ile Ile Tyr Ile Asp Asp Ala Lys Pro Thr Gln Asn Ser Leu
65                  70                  75                  80

Gly Leu Glu Leu Asp Asp Leu Ala Tyr Val Asn Tyr Ser Ser Gly Phe
                85                  90                  95

Leu Thr Arg Ser Pro Ala Leu Ile Leu Phe Phe Lys Asp Pro Ser Ser
            100                 105                 110

Ser Thr Glu Phe Val Gln Leu Ser Phe Arg Lys Ser Asp Gly Val Leu
        115                 120                 125

Phe Ser Gln Ala Thr Glu Arg Ala Leu Glu Asn Ile Leu Thr
    130                 135                 140

<210> SEQ ID NO 10
<211> LENGTH: 224
<212> TYPE: PRT
<213> ORGANISM: Artificial Sequence
<220> FEATURE:
<223> OTHER INFORMATION: Synthetic

<400> SEQUENCE: 10

Met Gln Leu Leu Ser Gly Ile Val Gln Gln Asn Asn Leu Leu Arg
1               5                   10                  15

Ala Ile Glu Ala Gln Gln His Leu Leu Gln Leu Thr Val Trp Gly Ile
            20                  25                  30

Lys Gln Leu Gln Ala Arg Ile Leu Ala Gly Gly Ser Gly Gly His Thr
        35                  40                  45

Thr Trp Met Glu Trp Asp Arg Glu Ile Asn Asn Tyr Thr Ser Leu Ile
    50                  55                  60

His Ser Leu Ile Glu Glu Ser Gln Asn Gln Gln Lys Asn Glu Gln
65                  70                  75                  80

Glu Leu Leu Glu Gly Ser Ser Gly Gly Gln Leu Leu Ser Gly Ile Val
                85                  90                  95

Gln Gln Gln Asn Asn Leu Leu Arg Ala Ile Glu Ala Gln Gln His Leu
            100                 105                 110

Leu Gln Leu Thr Val Trp Gly Ile Lys Gln Leu Gln Ala Arg Ile Leu
        115                 120                 125

Ala Gly Gly Ser Gly Gly His Thr Thr Trp Met Glu Trp Asp Arg Glu
    130                 135                 140

Ile Asn Asn Tyr Thr Ser Leu Ile His Ser Leu Ile Glu Glu Ser Gln
145                 150                 155                 160

Asn Gln Gln Glu Lys Asn Glu Gln Glu Leu Leu Glu Gly Ser Ser Gly
                165                 170                 175

Gly Gln Leu Leu Ser Gly Ile Val Gln Gln Asn Asn Leu Leu Arg
    180                 185                 190

Ala Ile Glu Ala Gln Gln His Leu Leu Gln Leu Thr Val Trp Gly Ile
        195                 200                 205

Lys Gln Leu Gln Ala Arg Ile Leu Ala Gly Gly His His His His
    210                 215                 220

<210> SEQ ID NO 11
<211> LENGTH: 185
<212> TYPE: PRT
<213> ORGANISM: Artificial Sequence
<220> FEATURE:
<223> OTHER INFORMATION: Synthetic

<400> SEQUENCE: 11

Met Gly Ser Ser His His His His His Ser Gln Asp Pro Gly Leu
1               5                   10                  15

Asn Asp Ile Phe Glu Ala Gln Lys Ile Glu Trp His Glu Gly Gly Ser
            20                  25                  30

Gly Gly Ser Gly Gly Thr Glu Tyr Trp His Tyr Val Glu Thr Thr Ser
        35                  40                  45

Ser Gly Gln Pro Leu Leu Arg Glu Gly Glu Lys Asp Ile Ala Ile Asp
    50                  55                  60

Gln Ser Val Gly Leu Tyr His Gly Lys Ser Lys Ile Leu Gln Arg Gln
65                  70                  75                  80

Arg Gly Arg Ile Phe Leu Thr Ser Gln Arg Ile Ile Tyr Ile Asp Asp
                85                  90                  95

Ala Lys Pro Thr Gln Asn Ser Leu Gly Leu Glu Leu Asp Asp Leu Ala
            100                 105                 110

Tyr Val Asn Tyr Ser Ser Gly Phe Leu Thr Arg Ser Pro Ala Leu Ile
        115                 120                 125

Leu Phe Phe Lys Asp Pro Ser Ser Thr Glu Phe Val Gln Leu Ser
    130                 135                 140

```
Phe Arg Lys Ser Asp Gly Val Trp Phe Ser Trp Ala Thr Glu Ile Ala
145                 150                 155                 160

Leu Tyr Thr Ile Leu Ile His Ser Leu Ile Glu Glu Ser Gln Asn Gln
                165                 170                 175

Gln Glu Lys Asn Glu Gln Glu Leu Leu
            180                 185
```

<210> SEQ ID NO 12
<211> LENGTH: 140
<212> TYPE: PRT
<213> ORGANISM: Artificial Sequence
<220> FEATURE:
<223> OTHER INFORMATION: Synthetic

<400> SEQUENCE: 12

```
Met Asp Tyr Lys Asp Asp Asp Lys Gly Gly Ser Glu Tyr Trp His
1               5                   10                  15

Tyr Val Glu Thr Thr Ser Ser Gly Gln Pro Leu Leu Arg Glu Gly Glu
                20                  25                  30

Lys Asp Ile Phe Ile Asp Gln Ser Val Gly Leu Tyr His Gly Lys Ser
            35                  40                  45

Lys Ile Leu Gln Arg Gln Arg Gly Arg Ile Phe Leu Thr Ser Gln Arg
        50                  55                  60

Ile Ile Tyr Ile Asp Asp Ala Lys Pro Thr Gln Asn Ser Leu Gly Leu
65                  70                  75                  80

Glu Leu Asp Asp Leu Ala Tyr Val Asn Tyr Ser Ser Gly Phe Leu Thr
                85                  90                  95

Arg Ser Pro Ala Leu Ile Leu Phe Phe Lys Asp Pro Ser Ser Ser Thr
            100                 105                 110

Glu Phe Val Gln Leu Ser Phe Arg Lys Ser Asp Gly Val Leu Phe Ser
        115                 120                 125

Gln Ala Thr Glu Arg Ala Leu Glu Asn Ile Leu Thr
    130                 135                 140
```

<210> SEQ ID NO 13
<211> LENGTH: 159
<212> TYPE: PRT
<213> ORGANISM: Artificial Sequence
<220> FEATURE:
<223> OTHER INFORMATION: Synthetic

<400> SEQUENCE: 13

```
Met Asp Tyr Lys Asp Asp Asp Lys Gly Gly Ser Glu Tyr Trp His
1               5                   10                  15

Tyr Val Glu Thr Thr Ser Ser Gly Gln Pro Leu Leu Arg Glu Gly Glu
                20                  25                  30

Lys Asp Ile Ala Ile Asp Gln Ser Val Gly Leu Tyr His Gly Lys Ser
            35                  40                  45

Lys Ile Leu Gln Arg Gln Arg Gly Arg Ile Phe Leu Thr Ser Gln Arg
        50                  55                  60

Ile Ile Tyr Ile Asp Asp Ala Lys Pro Thr Gln Asn Ser Leu Gly Leu
65                  70                  75                  80

Glu Leu Asp Asp Leu Ala Tyr Val Asn Tyr Ser Ser Gly Phe Leu Thr
                85                  90                  95

Arg Ser Pro Ala Leu Ile Leu Phe Phe Lys Asp Pro Ser Ser Ser Thr
            100                 105                 110

Glu Phe Val Gln Leu Ser Phe Arg Lys Ser Asp Gly Val Trp Phe Ser
```

```
                 115                 120                 125

Trp Ala Thr Glu Ile Ala Leu Tyr Thr Ile Leu Ile His Ser Leu Ile
    130                 135                 140

Glu Glu Ser Gln Asn Gln Gln Glu Lys Asn Glu Gln Glu Leu Leu
145                 150                 155

<210> SEQ ID NO 14
<211> LENGTH: 46
<212> TYPE: PRT
<213> ORGANISM: Artificial Sequence
<220> FEATURE:
<223> OTHER INFORMATION: Synthetic

<400> SEQUENCE: 14

Met Asp Tyr Lys Asp Asp Asp Lys Gly Gly Ser Trp Met Glu Trp
1               5                   10                  15

Asp Arg Glu Ile Asn Asn Tyr Thr Ser Leu Ile His Ser Leu Ile Glu
                20                  25                  30

Glu Ser Gln Asn Gln Gln Glu Lys Asn Glu Gln Glu Leu Leu
            35                  40                  45

<210> SEQ ID NO 15
<211> LENGTH: 179
<212> TYPE: PRT
<213> ORGANISM: Artificial Sequence
<220> FEATURE:
<223> OTHER INFORMATION: Synthetic

<400> SEQUENCE: 15

Met Gly Ser Ser His His His His His His Ser Ser Gly Leu Val Pro
1               5                   10                  15

Arg Gly Ser His Met Asp Tyr Lys Asp Asp Asp Lys Gly Gly Ser
                20                  25                  30

Glu Tyr Trp His Tyr Val Glu Thr Thr Ser Ser Gly Gln Pro Leu Leu
            35                  40                  45

Arg Glu Gly Glu Lys Asp Ile Ala Ile Asp Gln Ser Val Gly Leu Tyr
    50                  55                  60

His Gly Lys Ser Lys Ile Leu Gln Arg Gln Arg Gly Arg Ile Phe Leu
65                  70                  75                  80

Thr Ser Gln Arg Ile Ile Tyr Ile Asp Asp Ala Lys Pro Thr Gln Asn
                85                  90                  95

Ser Leu Gly Leu Glu Leu Asp Asp Leu Ala Tyr Val Asn Tyr Ser Ser
            100                 105                 110

Gly Phe Leu Thr Arg Ser Pro Ala Leu Ile Leu Phe Phe Lys Asp Pro
        115                 120                 125

Ser Ser Ser Thr Glu Phe Val Gln Leu Ser Phe Arg Lys Ser Asp Gly
    130                 135                 140

Val Trp Phe Ser Trp Ala Thr Glu Ile Ala Leu Tyr Thr Ile Leu Ile
145                 150                 155                 160

His Ser Leu Ile Glu Glu Ser Gln Asn Gln Gln Glu Lys Asn Glu Gln
                165                 170                 175

Glu Leu Leu

<210> SEQ ID NO 16
<211> LENGTH: 242
<212> TYPE: PRT
<213> ORGANISM: Artificial Sequence
<220> FEATURE:
<223> OTHER INFORMATION: Synthetic
```

<400> SEQUENCE: 16

Met Glu Tyr Trp His Tyr Val Glu Thr Thr Ser Ser Gly Gln Pro Leu
1               5                   10                  15

Leu Arg Glu Gly Glu Lys Asp Ile Ala Ile Asp Gln Ser Val Gly Leu
            20                  25                  30

Tyr His Gly Lys Ser Lys Ile Leu Gln Arg Gln Arg Gly Arg Ile Phe
        35                  40                  45

Leu Thr Ser Gln Arg Ile Ile Tyr Ile Asp Asp Ala Lys Pro Thr Gln
50                  55                  60

Asn Ser Leu Gly Leu Glu Leu Asp Asp Leu Ala Tyr Val Asn Tyr Ser
65                  70                  75                  80

Ser Gly Phe Leu Thr Arg Ser Pro Ala Leu Ile Leu Phe Phe Lys Asp
                85                  90                  95

Pro Ser Ser Ser Thr Glu Phe Val Gln Leu Ser Phe Arg Lys Ser Asp
            100                 105                 110

Gly Val Trp Phe Ser Trp Ala Thr Glu Ile Ala Leu Tyr Thr Ile Leu
        115                 120                 125

Ile His Ser Leu Ile Glu Glu Ser Gln Asn Gln Gln Glu Lys Asn Glu
130                 135                 140

Gln Glu Leu Leu Gly Gly Ser Gly Gly Ser Gly Thr Ser Gly Gly Ser
145                 150                 155                 160

Gly Lys Asn Gly Ile Lys Ala Lys Phe Lys Ile Arg His Asn Val Lys
                165                 170                 175

Asp Gly Ser Val Gln Leu Ala Asp His Tyr Gln Gln Asn Thr Pro Ile
            180                 185                 190

Gly Arg Gly Pro Val Leu Leu Pro Arg Asn His Tyr Leu Ser Thr Arg
        195                 200                 205

Ser Lys Leu Ser Lys Asp Pro Lys Glu Lys Arg Asp His Met Val Leu
210                 215                 220

Leu Glu Phe Val Thr Ala Ala Gly Ile Lys His Gly Arg Asp Glu Arg
225                 230                 235                 240

Tyr Lys

<210> SEQ ID NO 17
<211> LENGTH: 130
<212> TYPE: PRT
<213> ORGANISM: Artificial Sequence
<220> FEATURE:
<223> OTHER INFORMATION: Synthetic

<400> SEQUENCE: 17

Met Gly Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Gly Gly Ser Gly Gly Ser Gly Thr Ser Gly Gly Ser
        35                  40                  45

Gly Lys Asn Gly Ile Lys Ala Lys Phe Lys Ile Arg His Asn Val Lys
50                  55                  60

Asp Gly Ser Val Gln Leu Ala Asp His Tyr Gln Gln Asn Thr Pro Ile
65                  70                  75                  80

Gly Arg Gly Pro Val Leu Leu Pro Arg Asn His Tyr Leu Ser Thr Arg
                85                  90                  95

Ser Lys Leu Ser Lys Asp Pro Lys Glu Lys Arg Asp His Met Val Leu

```
                     100                 105                 110

Leu Glu Phe Val Thr Ala Ala Gly Ile Lys His Gly Arg Asp Glu Arg
        115                 120                 125

Tyr Lys
    130

<210> SEQ ID NO 18
<211> LENGTH: 402
<212> TYPE: PRT
<213> ORGANISM: Artificial Sequence
<220> FEATURE:
<223> OTHER INFORMATION: Synthetic

<400> SEQUENCE: 18

Met Gly His His His His His Gly Gly Ala Ser Lys Gly Glu Arg
1               5                   10                  15

Leu Phe Arg Gly Lys Val Pro Ile Leu Val Glu Leu Lys Gly Asp Val
            20                  25                  30

Asn Gly His Lys Phe Ser Val Arg Gly Glu Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Gly Gly Ser Gly Ser Gly Ser Ser Gly
                165                 170                 175

Gly Thr Gln Leu Leu Ser Gly Ile Val Gln Gln Gln Asn Asn Leu Leu
            180                 185                 190

Arg Ala Ile Glu Ala Gln Gln His Leu Leu Gln Leu Thr Val Trp Gly
        195                 200                 205

Ile Lys Gln Leu Gln Ala Arg Ile Leu Ala Gly Gly Ser Gly Gly His
    210                 215                 220

Thr Thr Trp Met Glu Trp Asp Arg Glu Ile Asn Asn Tyr Thr Ser Leu
225                 230                 235                 240

Ile His Ser Leu Ile Glu Glu Ser Gln Asn Gln Gln Glu Lys Asn Glu
                245                 250                 255

Gln Glu Leu Leu Glu Gly Ser Ser Gly Gly Leu Leu Ser Gly Ile
            260                 265                 270

Val Gln Gln Gln Asn Asn Leu Leu Arg Ala Ile Glu Ala Gln Gln His
        275                 280                 285

Leu Leu Gln Leu Thr Val Trp Gly Ile Lys Gln Leu Gln Ala Arg Ile
    290                 295                 300

Leu Ala Gly Gly Ser Gly Gly His Thr Thr Trp Met Glu Trp Asp Arg
305                 310                 315                 320

Glu Ile Asn Asn Tyr Thr Ser Leu Ile His Ser Leu Ile Glu Glu Ser
```

```
                    325                 330                 335
Gln Asn Gln Gln Glu Lys Asn Glu Gln Glu Leu Leu Glu Gly Ser Ser
                340                 345                 350
Gly Gly Gln Leu Leu Ser Gly Ile Val Gln Gln Gln Asn Asn Leu Leu
                355                 360                 365
Arg Ala Ile Glu Ala Gln Gln His Leu Leu Gln Leu Thr Val Trp Gly
            370                 375                 380
Ile Lys Gln Leu Gln Ala Arg Ile Leu Ala Gly Gly His His His His
385                 390                 395                 400
His His

<210> SEQ ID NO 19
<211> LENGTH: 148
<212> TYPE: PRT
<213> ORGANISM: Artificial Sequence
<220> FEATURE:
<223> OTHER INFORMATION: Synthetic

<400> SEQUENCE: 19

Met Glu Tyr Trp His Tyr Val Glu Thr Thr Ser Ser Gly Gln Pro Leu
1               5                   10                  15
Leu Arg Glu Gly Glu Lys Asp Ile Ala Ile Asp Gln Ser Val Gly Leu
                20                  25                  30
Tyr His Gly Lys Ser Lys Ile Leu Gln Arg Gln Arg Gly Arg Ile Phe
            35                  40                  45
Leu Thr Ser Gln Arg Ile Ile Tyr Ile Asp Asp Ala Lys Pro Thr Gln
        50                  55                  60
Asn Ser Leu Gly Leu Glu Leu Asp Asp Leu Ala Tyr Val Asn Tyr Ser
65                  70                  75                  80
Ser Gly Phe Leu Thr Arg Ser Pro Ala Leu Ile Leu Phe Phe Lys Asp
                85                  90                  95
Pro Ser Ser Ser Thr Glu Phe Val Gln Leu Ser Phe Arg Lys Ser Asp
                100                 105                 110
Gly Val Trp Phe Ser Trp Ala Thr Glu Ile Ala Leu Tyr Thr Ile Leu
            115                 120                 125
Ile His Ser Leu Ile Glu Glu Ser Gln Asn Gln Gln Glu Lys Asn Glu
        130                 135                 140
Gln Glu Leu Leu
145
```

HELIX-GRAFTED PROTEINS AS INHIBITORS OF DISEASE-RELEVANT PROTEIN-PROTEIN INTERACTIONS

CROSS REFERENCE TO RELATED APPLICATIONS

This application is a divisional application of U.S. application Ser. No. 14/936,200 filed Nov. 9, 2015, which application claims the benefit of U.S. Provisional Application No. 62/076,959, filed Nov. 7, 2014. The disclosures of both above-referenced applications are hereby incorporated by reference in their entirety.

SEQUENCE LISTING

A Sequence Listing submitted in computer readable form (CRF) is hereby incorporated by reference. The CRF file named CSURF15-019_SeqListing_ST25.txt, was created on Feb. 5, 2016, and contains 22 kilobytes.

FIELD OF THE INVENTION

The disclosure provides helix grafted proteins, methods of producing helix grafted proteins and methods of use of helix grafted proteins as inhibitors of protein-protein interactions involved in disease pathogenesis.

BACKGROUND OF THE INVENTION

HIV-1 is a notorious human pathogen that affects ~35 million people worldwide. HIV-1 is considered an enveloped virus because its nucelocapsid, which contains the viral genome, is surrounded by a lipid membrane. Membrane fusion of HIV-1 is mediated by the glycoprotein, gp160. gp160 is cleaved by a protease into two noncovalently bonded glycoproteins; gp120 and gp41. gp120, the surface subunit, is essential for recognizing the target cell's surface receptor. gp41, the transmembrane subunit, contains several regions that are responsible for the merge of the viral membrane and the target cell membrane. The fusion peptide, FP, is important for inducing viral entry, promoted by anchoring itself into the host membrane. X-ray crystallography shows that the C- and N-terminal heptad repeats (CHR and NHR) exist as a trimer of hairpins, in one of its final fusion conformations. NHR is able to self-interact forming a central trimeric coiled-coil with three large hydrophobic pockets. The three helical CHR peptides are able to bind NHR in an antiparallel fashion. This formation, referred to as the 6-helix bundle (6HB), is key for successful infection.

α-Helical peptides mimicking NHR and CHR of gp41 are a validated therapeutic approach for membrane fusion. NHR peptides are able to inhibit infection with micromolar concentrations but often aggregate because of their hydrophobic residues. CHR peptides (also referred to as C-peptides) have proven to be more potent and effective than NHR peptides. For example, C34 (residues 628-661 of CHR) is effective at inhibiting HIV-1 viral membrane fusion in nanomolar concentrations. Despite their success, α-helical peptides still have considerable drawbacks, namely cost of production and sensitivity to degradation. Proteolytic stability is a common issue for α-helical peptides because they are often found disordered in solution, which makes them susceptible to degradation thereby limiting their potency in vivo. Thus, there is a need in the art for new strategies to stabilize α-helical peptides.

SUMMARY OF THE INVENTION

In one aspect, the disclosure provides a helix grafted protein comprising all or a portion of a C-peptide from a virus grafted onto a terminal helix of a protein containing one or more Pleckstrin homology (PH) domain and/or PH-like domain.

In another aspect, the disclosure provides a method of producing a helix grafted protein comprising: aligning a terminal helix on a protein containing one or more Pleckstrin homology (PH) domain or PH-like domain with a C-peptide from a virus; selecting positions on the terminal helix to install residues from the C-peptide sequence in such a way as to preserve the three-dimensional confirmation of the residues from the C-peptide to generate a grafted helix; and extending the grafted helix by attaching C-peptide residues to the terminus of the grafted helix, thereby producing the helix grafted protein.

In still another aspect, the disclosure provides a method of inhibiting entry of virus into cells of a subject, the method comprising administering to the subject a composition comprising a helix grafted protein comprising all or a portion of a C-peptide from a virus grafted onto a terminal helix of a protein containing one or more Pleckstrin homology (PH) domain or PH-like domain.

The PH-like domain may be a phosphotyrosine-binding (PTB) domain. The protein containing one or more Pleckstrin homology (PH) domain and/or PH-like domain may be selected from the group consisting of GLUE, HOMER, PLECKSTRIN, AKT2, DOK5, and ELMO. The protein containing one or more Pleckstrin homology (PH) domain and/or PH-like domain may be selected from the group consisting of GLUE and ELMO.

The C-peptide may be a gp41 C-peptide. The gp41 C-peptide may comprise SEQ ID NO:2 (WMEWDREINNYTSLIHSLIEESQNQQEKNEQELL).

The protein containing one or more PH domain and/or PH-like domain may be GLUE and the C-peptide grafted onto the terminal helix of GLUE may comprise SEQ ID NO:3 (GVWFSWATEIALYTILIHSLIEESQNQQEKNEQELL). The protein containing one or more PH domain and/or PH-like domain may be ELMO and the C-peptide grafted onto the N-terminal helix of ELMO may comprise SEQ ID NO:7 (WMEWDREINNYTSLIHSLIEESQNQQKQQRLNRLVE). The protein containing one or more PH domain and/or PH-like domain may be ELMO and the C-peptide grafted onto the C-terminal helix of ELMO may comprise SEQ ID NO:8 (DKWEYWIWTIGLYTLLGKSLIEESQNQQEKNEQELL).

BRIEF DESCRIPTION OF THE FIGURES

The application file contains at least one drawing executed in color. Copies of this patent application publication with color drawing(s) will be provided by the Office upon request and payment of the necessary fee.

FIG. 1A depicts a schematic of HIV viral fusion by formation of a trimer-of-hairpins assembly involving the N-terminal helical region (NHR, orange) and the C-terminal helical region (CHR, purple) of gp41.

FIG. 1B depicts a crystal structure of the NHR/CHR complex (PDB ID: 1AIK).

FIG. 2A and FIG. 2B depict helix-grafting HIV gp41 C-peptide helix onto a stable PH-like domain protein. FIG. 2A depicts wild-type GLUE (gray) and gp41 C-peptide (dark blue). Sequences of the GLUE helix (SEQ ID NO:1—GVLFSQATERALENILT) and the corresponding region of the gp41 helix (SEQ ID NO:2—WMEWDREINNYTS-LIHSLIEESQNQQEKNEQELL) are shown in gray and blue, respectively. Spheres indicate the Cα positions for each. FIG. 2B depicts helix-grafted GLUE-Cpep (SEQ ID NO:3—GVWFSWATEIALYTILIHSLIEESQNQQEK-NEQELL), produced by backbone alignment of the independent structures. Spheres indicate Cα positions of GLUE residues mutated to those from gp41 (also color coded in the sequence).

FIG. 3A depicts circular dichroism data for wtGLUE (red) and GLUE-Cpep (blue).

FIG. 3B depicts a Western blot of FLAG-tagged helix-grafted GLUE not incubated with human serum (lane 1), and after incubation with human serum for 0.5 to 12 h (lanes 2-7).

Figure 4A:
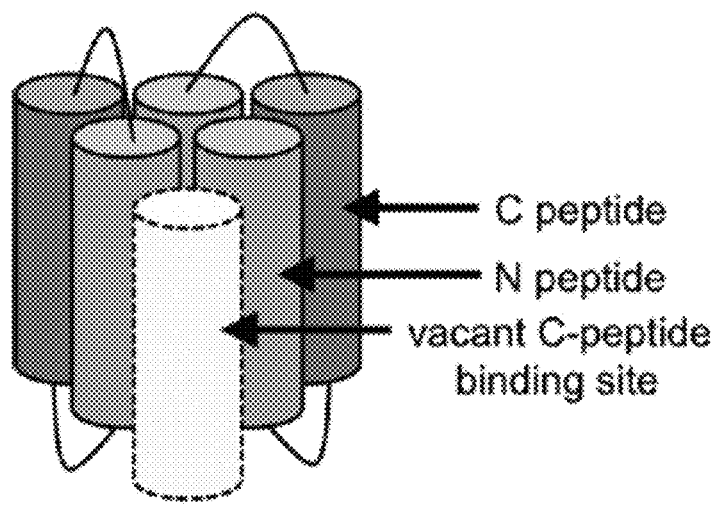
FIG. 4A depicts a 5-helix, a single protein consisting of three copies of gp41 N-peptide (orange) and two copies of gp41 C-peptide (purple). When folded, this protein presents a single binding site for a C-peptide (or mimic thereof), which is depicted as a gray column with dashed border.
Figure 4B:
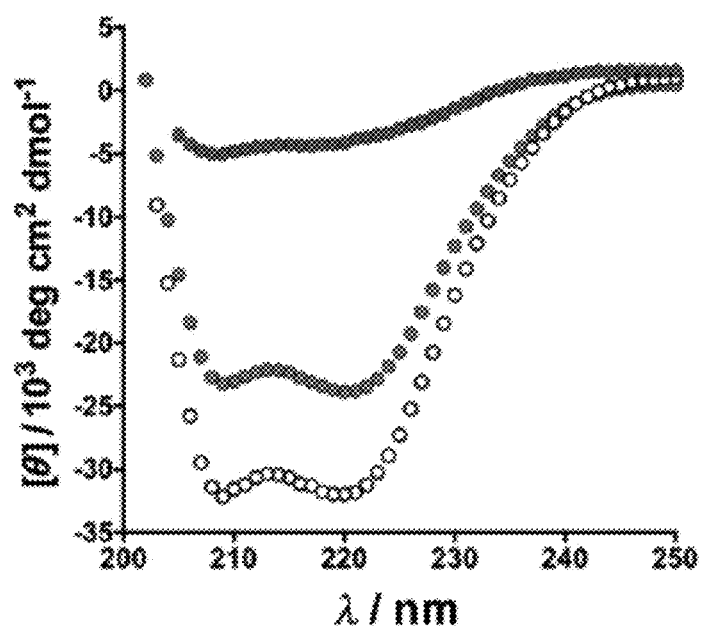
FIG. 4B depicts circular dichroism spectra of GLUE-Cpep (blue), 5-helix (red), and a pre-mixed 1:1 ratio of 5-helix and GLUE-Cpep (white).
Figure 4C:
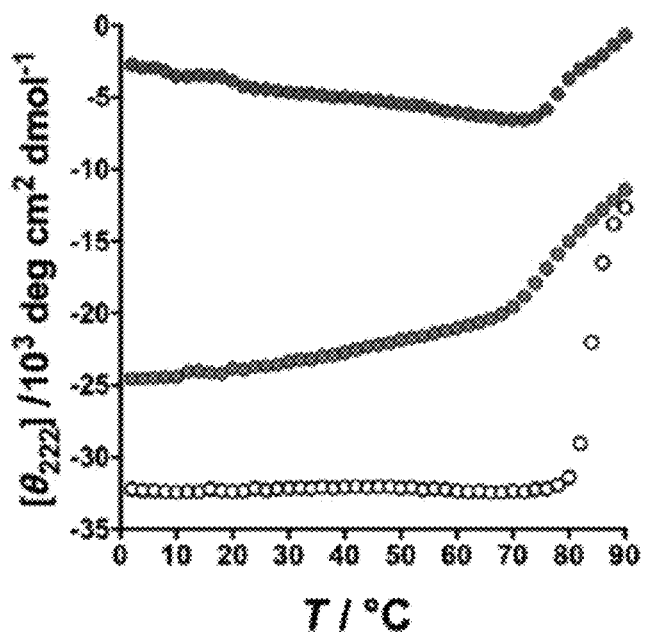
FIG. 4C depicts CD data (222 nm) showing temperature-dependent melting of the solutions in FIG. 4B.
Figure 4D:
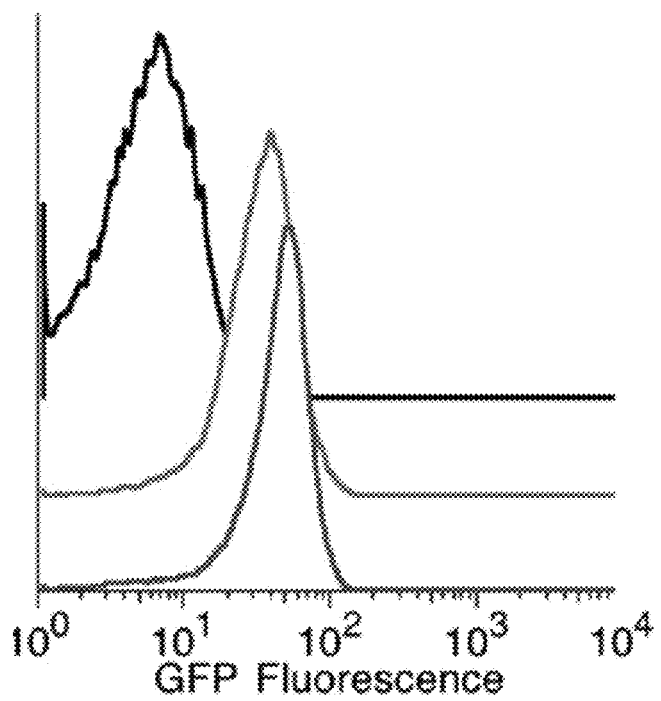

FIG. 4D depicts flow cytometry data for E. coli following split-spGFP reassembly experiments. B lack: NspGFP-5-helix/CspGFP, Red: NspGFP-5-helix/CspGFP-Cpep; Blue: NspGFP-5-helix/CspGFP-GLUE-Cpep.

Figure 4E:
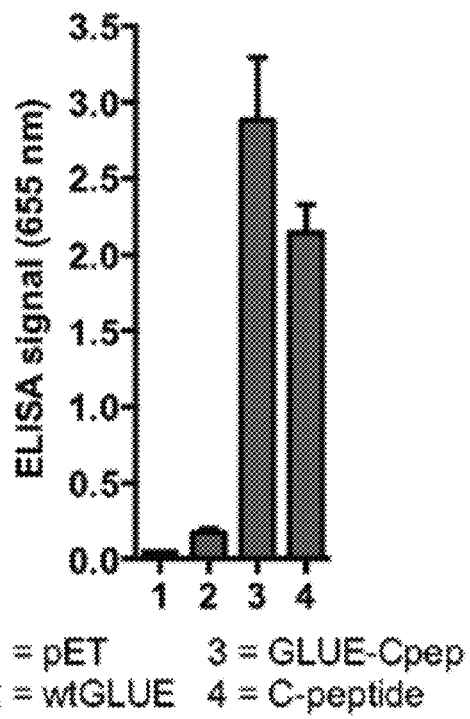

FIG. 4E depicts ELISA data from E. coli cell lysate that contains an empty pET DUET plasmid, or pET DUET that encodes $His_6$-tagged 5-helix, along with wtGLUE, grafted GLUE, or C-peptide.

Figure 4F:
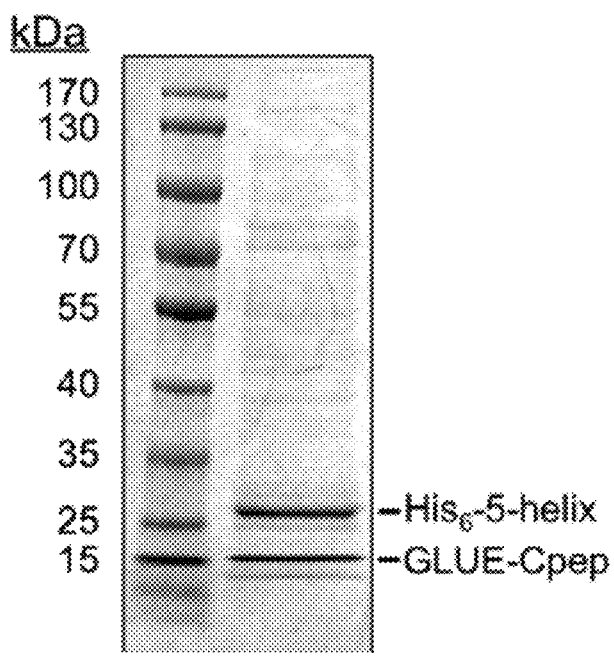

FIG. 4F depicts copurification of $His_6$-tagged 5-helix and untagged GLUE-Cpep from E. coli cell lysate.

Figure 5A:
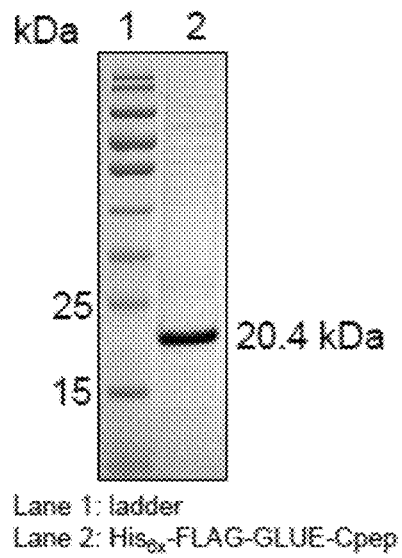
Figure 5B:
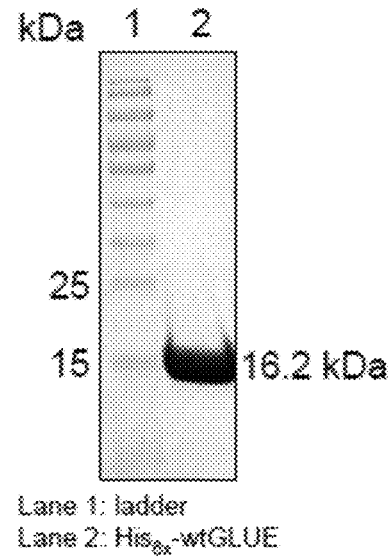
Figure 5C:
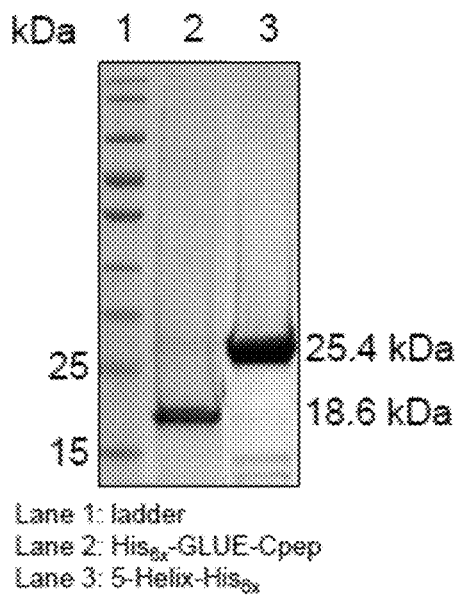
Figure 5D:
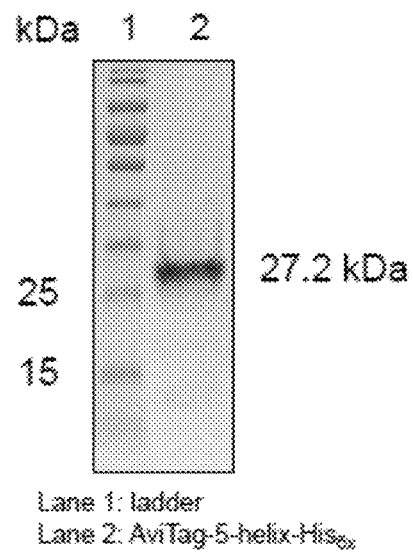

FIG. 5A, FIG. 5B, FIG. 5C and FIG. 5D depict purified proteins used in this work. FIG. 5A depicts PAGE gel of coomassie stained His6×-FLAG-GLUE-Cpep. FIG. 5B depicts PAGE gel of coomassie stained His6×-wtGLUE. FIG. 5C depicts PAGE gel of coomassie stained His6×-GLUE-Cpep (lane 2) and 5 Helix-His6× (lane 3). FIG. 5D depicts PAGE Gels of coomassie stained AviTag-5-helix-His6×.

Figure 6:
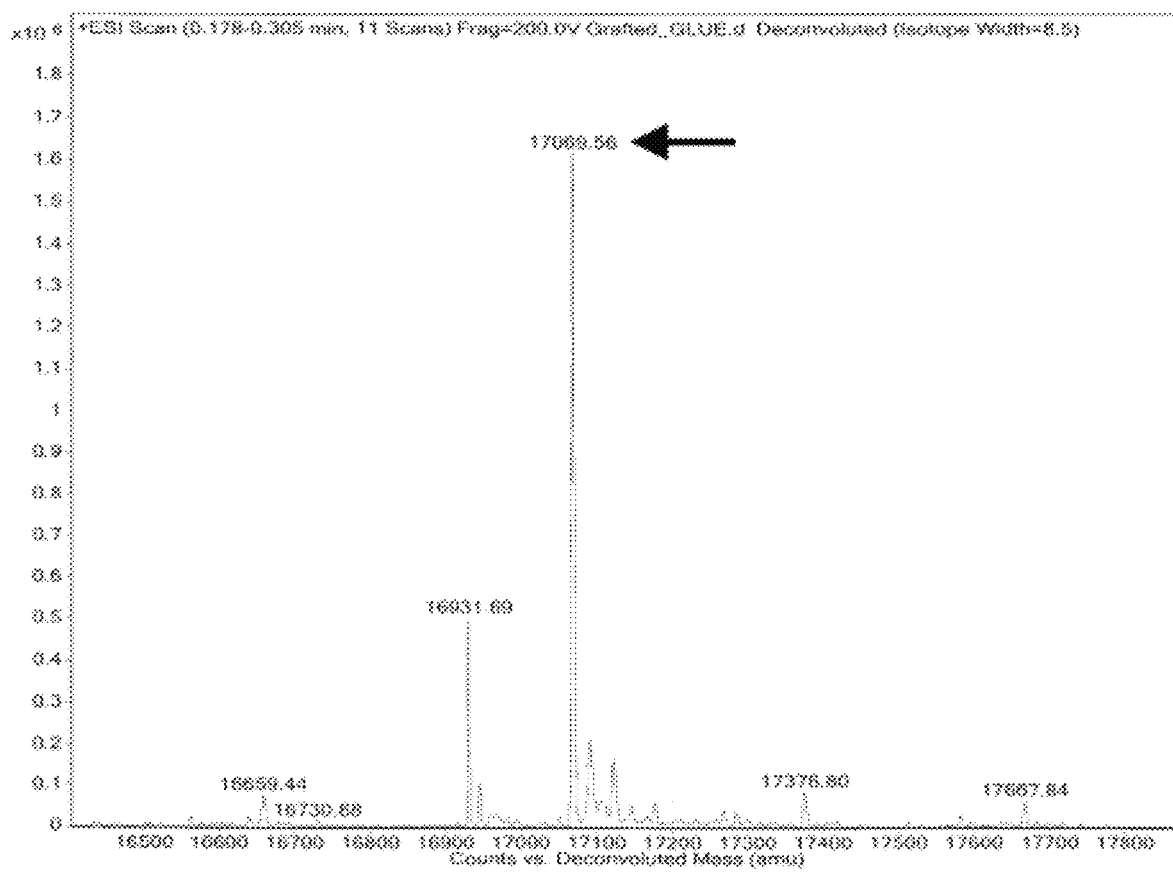

FIG. 6 depicts mass of protein (GLUE-Cpep) that is co-purified with His6×-5-helix. Expected mass (GLUE-Cpep)=17,069 Da [M+1]; Observed mass=17,069 Da.

Figure 7A:
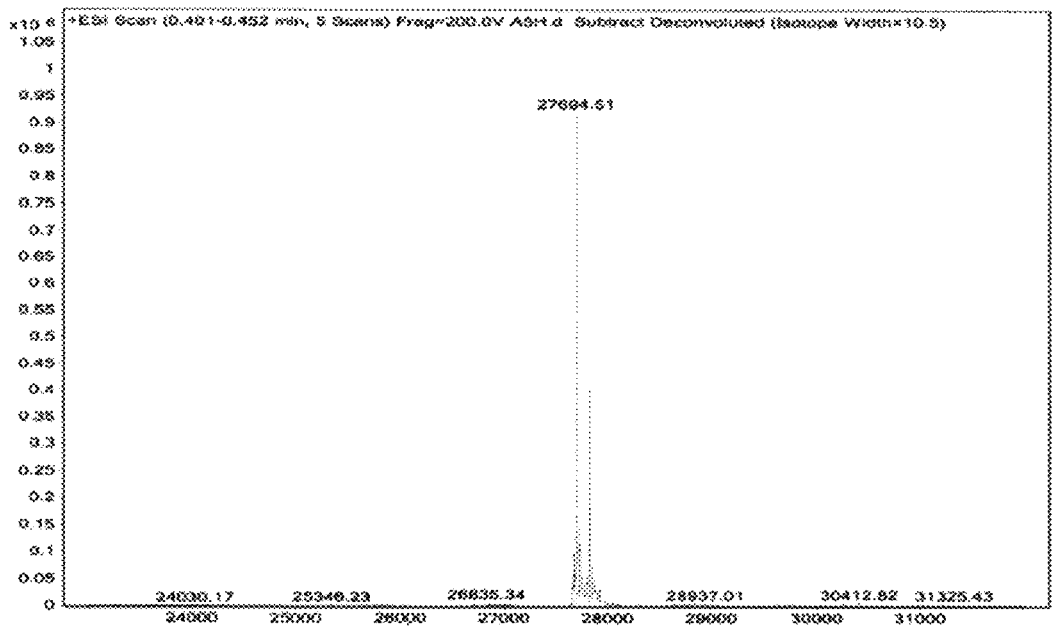
Figure 7B:
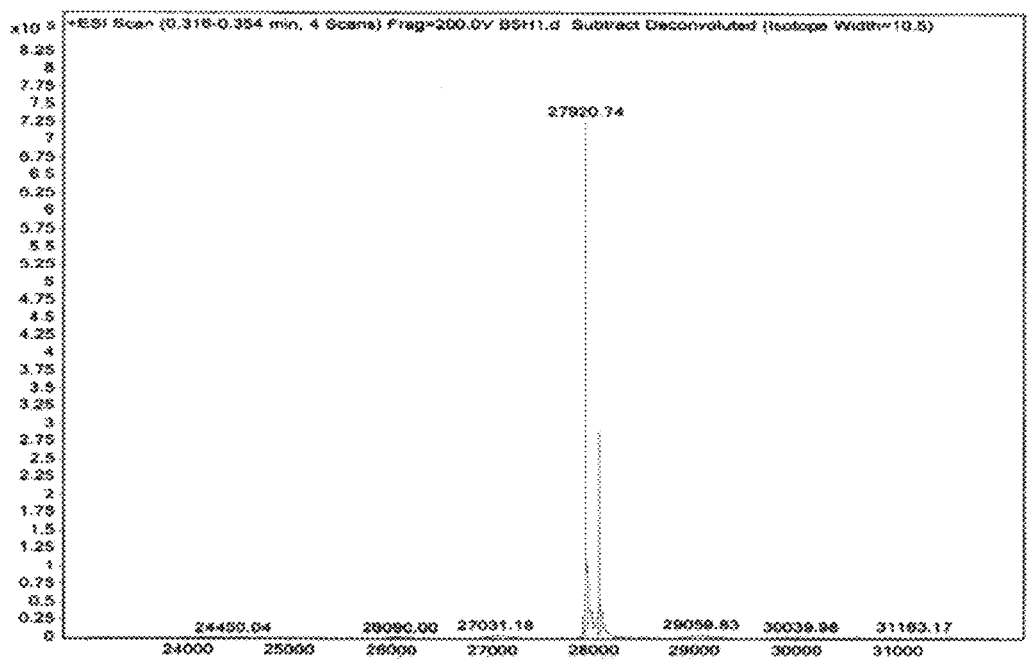

FIG. 7A and FIG. 7B depict biotinylation of AviTagged 5-helix and ELISA in human serum. Biotinylation of Avi-Tag-5-helix-His6× with BirA. (FIG. 7A) Expected mass (GLUE-Cpep)=27,694 Da [M+1]; Observed mass=27,694 Da. (FIG. 7B) Expected mass (GLUE-Cpep)=27,920 Da [M+1]; Observed mass=27,920 Da.

FIG. 8 depicts ELISA data in human serum. Negative=no protein is immobilized on the plate.

FIG. 9A depicts a schematic representation of the essential regions for HIV-1 gp41 membrane fusion and their amino acid sequence. (SEQ ID NO: 4—AVGIGALGLGFL-GAAGSTMGAASMTLTVQARQLLSGIVQQQNNLL-RAIEAQQHLLQLT VWGIKQLQARILAVERY-LKDQQLLGIQGCSKLICTTAVPWNASWSKSLEQIWH NHTTW MEWDREINNYTSLIHSLIEESQNQQEK-NEQELLELDKWASLWNWFNITNWLWYIK).

FIG. 9B depicts a 6HB cartoon, PDB code 1aik.

Figure 10:
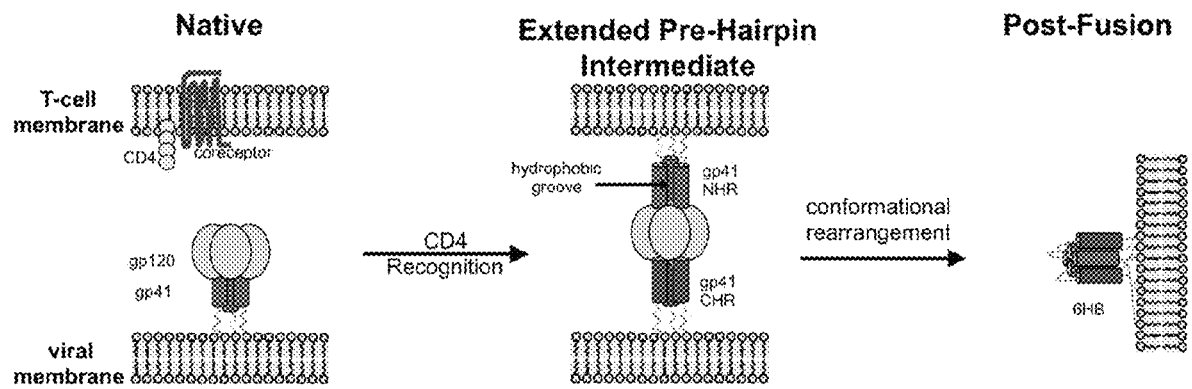

FIG. 10 depicts a schematic of HIV-1 viral membrane fusion. Three important confirmations are highlighted. Potential inhibitors are predicted to bind the hydrophobic groove in the extended pre-hairpin intermediate.

Figure 11:
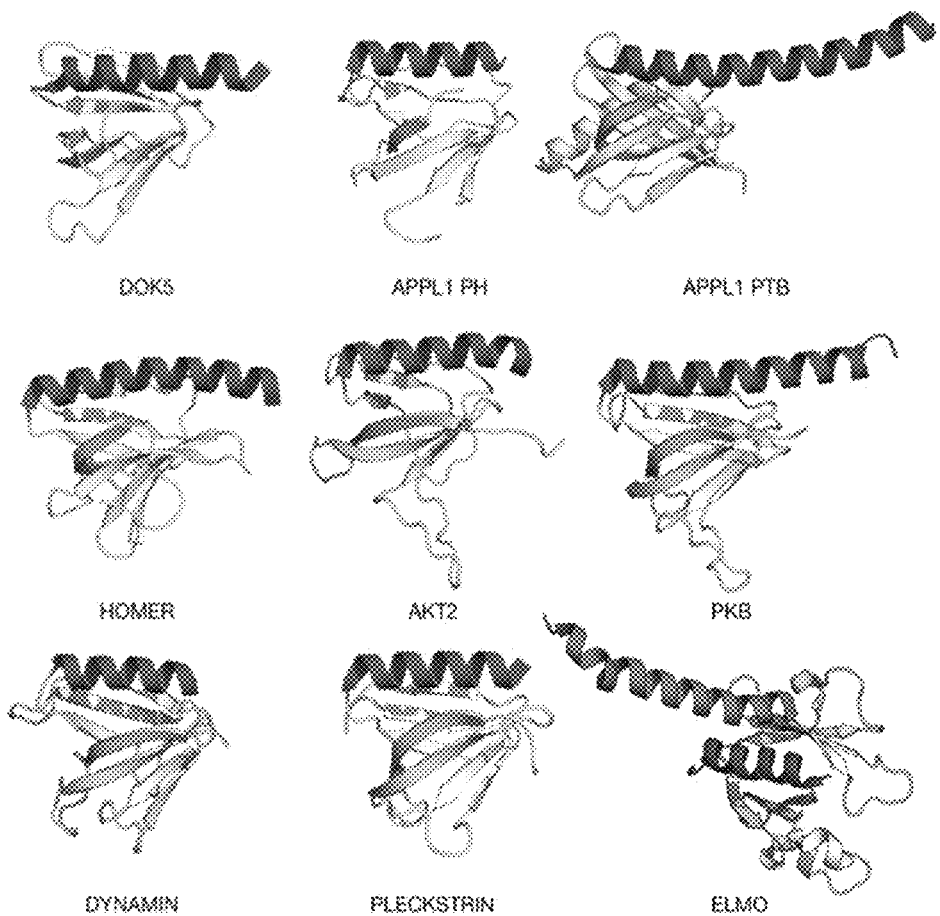

FIG. 11 depicts candidate PH domains for helix grafted display of HIV-1 gp41 C-peptide.

Figure 12A:
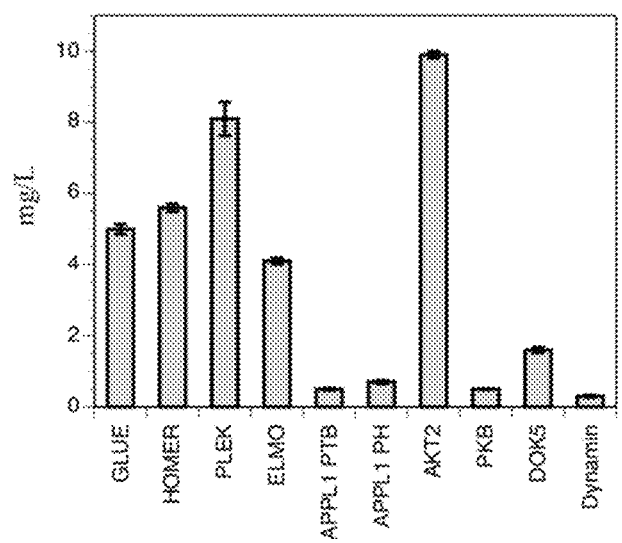

FIG. 12A depicts quantification of PH domain expression in mg/L. Each protein was recombinantly expressed, grown up and purified under the same conditions. Data was done in triplicate.

Figure 12B:
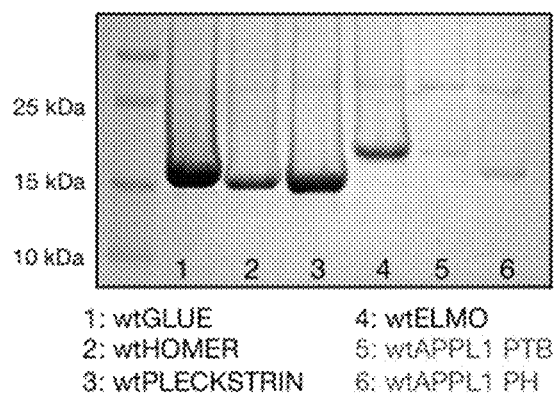
Figure 12C:
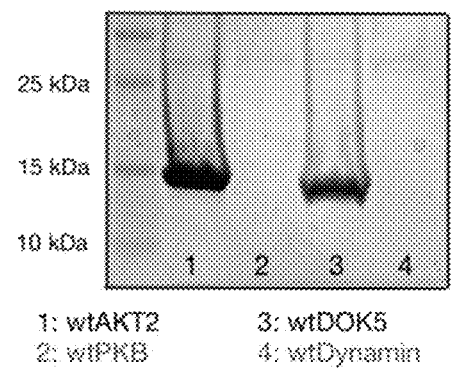

FIG. 12B and FIG. 12C depict purified proteins run on a PAGE gel to confirm size and visualization of their solubility. Scaffolds highlighted in green were eliminated.

FIG. 13 depicts a diagram of helix grafted display of C-peptide (top, pink) onto both ELMO helices (orange and blue, bottom). Sequences are shown below each construct. C-peptide: SEQ ID NO:2—WMEWDREINNYTS-LIHSLIEESQNQQEKNEQELL; N-terminal ELMO: SEQ ID NO:5—PILELKEKIQPEILELIKQQRLNRLVE; C-terminal ELMO: SEQ ID NO:6—DKHEYCIWTDG-LNALLGK; C26-ELMO: SEQ ID NO:7—WMEWDREIN-NYTSLIHSLIEESQNQQKQQRLNRLVE; and ELMO-C34: SEQ ID NO:8—DKWEYWIWTIG-LYTLLGKSLIEESQNQQEKNEQELL.

FIG. 14A depicts quantification of grafted scaffolds in mg/L. Each protein was recombinantly expressed, grown up and purified under the same conditions. Data was done in triplicate.

FIG. 14B depicts purified proteins run on an SDS PAGE gel. Grafted scaffolds highlighted in green were eliminated.

Figure 15A:
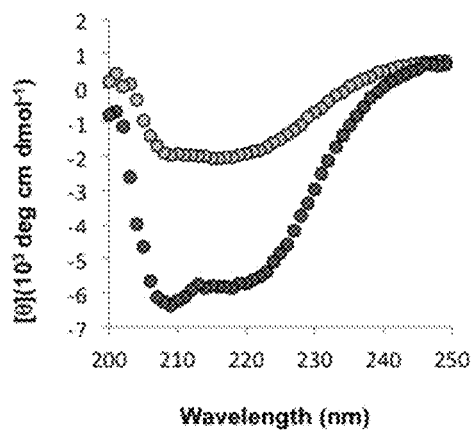

FIG. 15A depicts the CD wavelength scans for C26-ELMO and wtELMO.

Figure 15B:
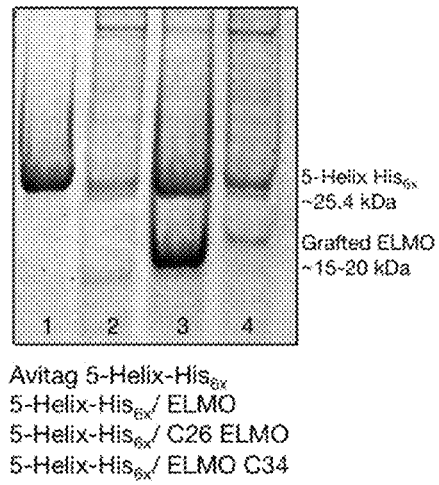

FIG. 15B depicts copurification of $His_6$-tagged 5-helix and untagged grafted ELMO from E. coli cell lysate.

Figure 15C:
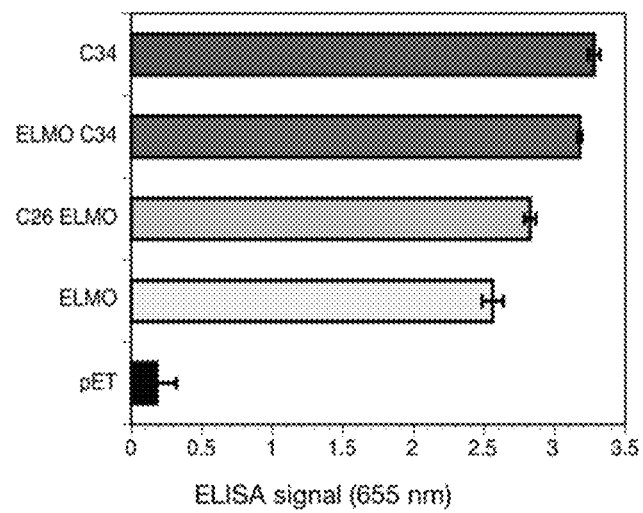

FIG. 15C depicts ELISA data from E. coli cell lysate that contains an empty pET DUET plasmid, or pET DUET that encodes $His_6$-tagged 5-helix, along with ELMO, C26 ELMO, ELMO C34 and C34.

Figure 16A:
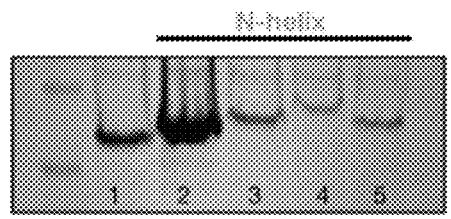
Figure 16B:
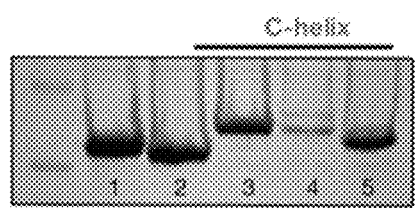

FIG. 16A and FIG. 16B depict protein gels showing expression of grafted ELMO proteins in pET DUET.

Figure 17A:
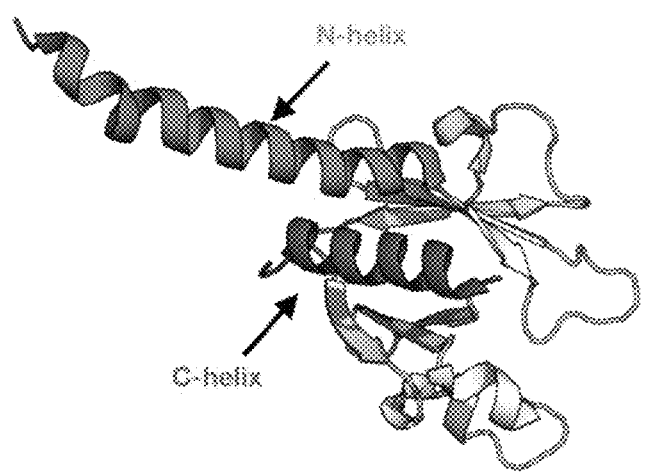

FIG. 17A depicts the crystal structure of ELMO, PDB code 2vsz.

Figure 17B:
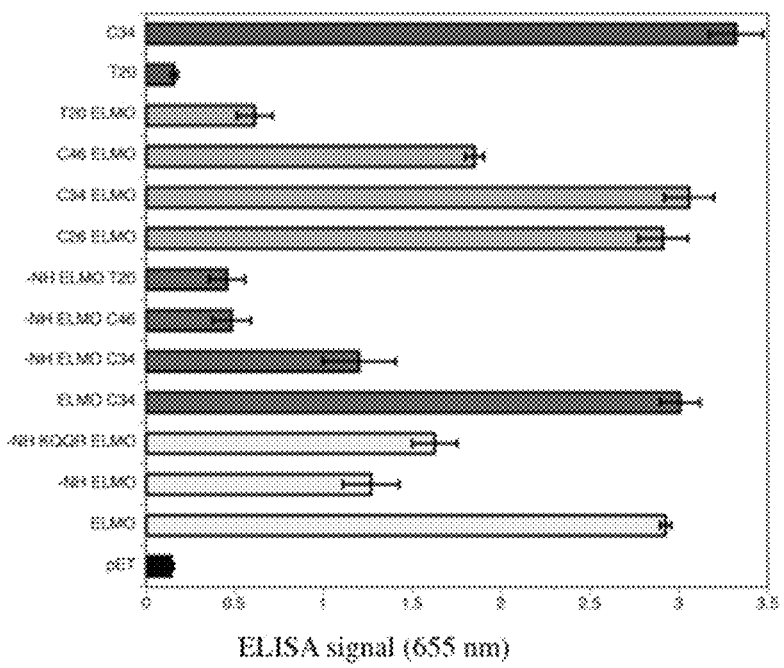

FIG. 17B depicts ELISA data from E. coli cell lysate that contain an empty pETDuet plasmid, or pETDuet that encodes His6×-tagged 5-helix along with wtELMO, grafted ELMO constructs, or C-peptide.

Figure 17C:
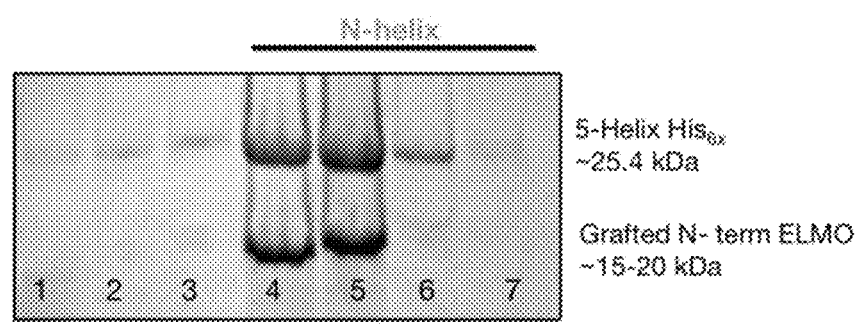
Figure 17D:
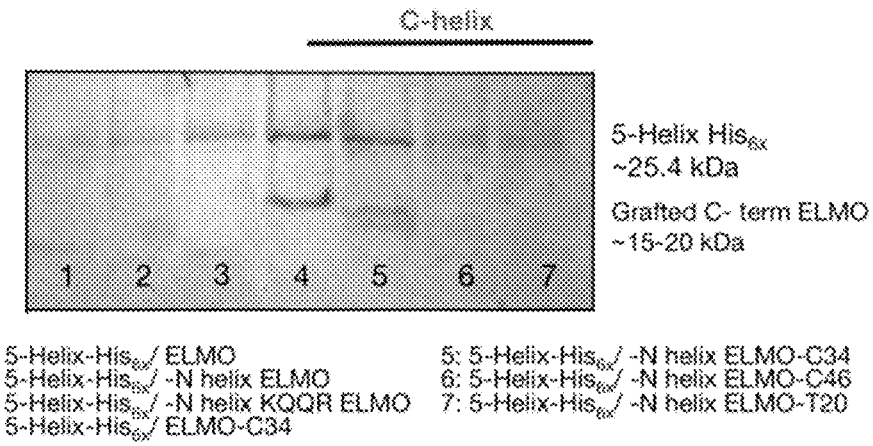

FIG. 17C and FIG. 17D depict co-purification of His6×-tagged 5-helix and untagged ELMO grafts from E. coli cell lysate.

Figure 18:
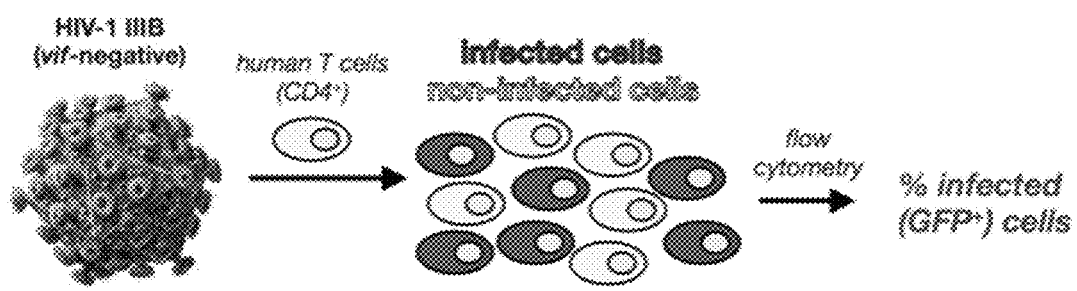

FIG. 18 is a cartoon depicting the in cellulo HIV-1 infection assay.

Figure 19A:
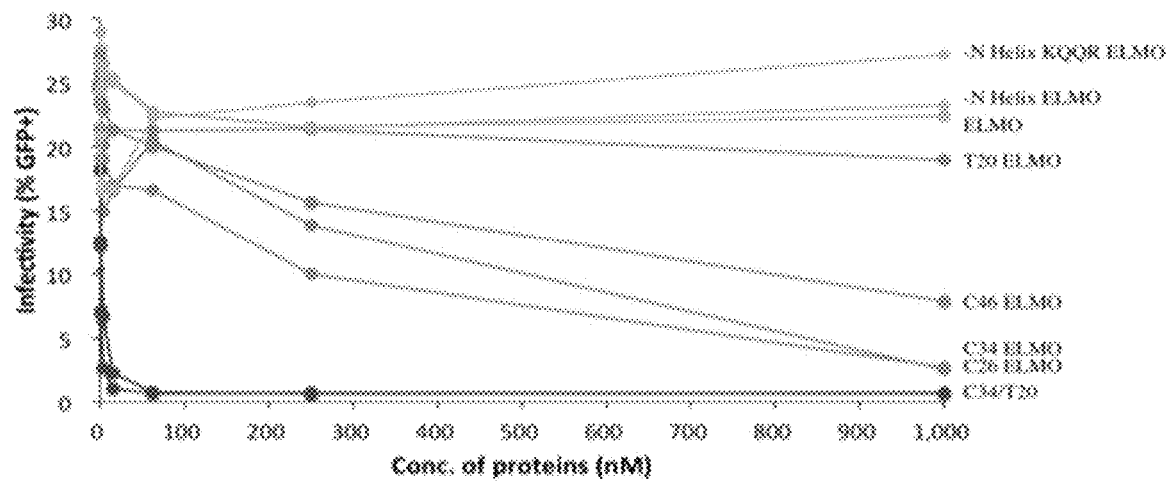
Figure 19B:
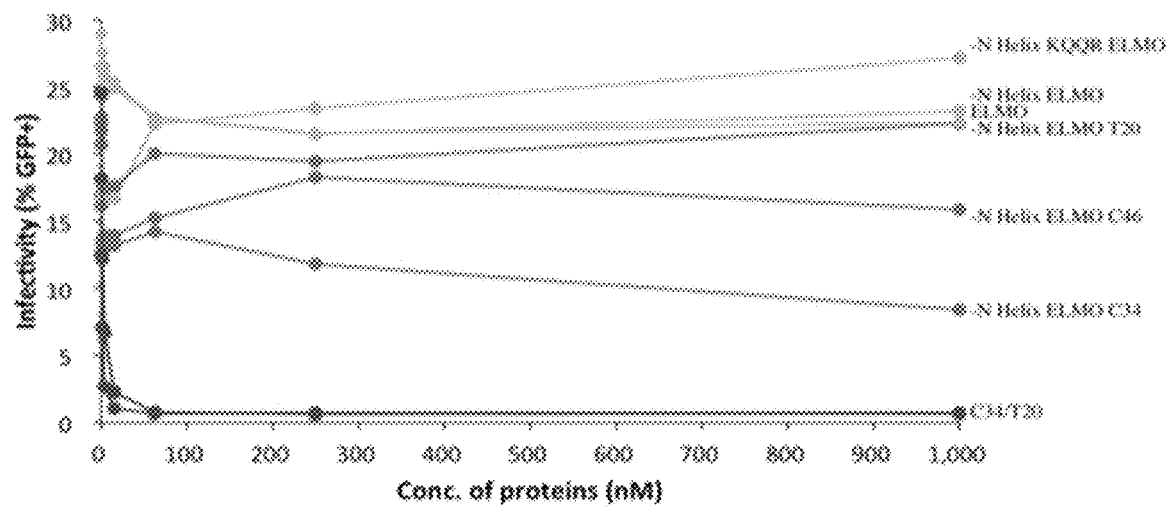

FIG. 19A and FIG. 19B depict infectivity results for N-terminal (FIG. 19A) and C-terminal (FIG. 19B) ELMO grafts compared to C34 and T20 peptides.

DETAILED DESCRIPTION OF THE INVENTION

Described herein are helix grafted proteins comprising all or a portion of a C-peptide (e.g., from a virus) and a polypeptide scaffold. Particularly, the C-peptide comprises a stable helical structure. When the C-peptide is from a virus it can act as a potent inhibitor of viral entry and has improved resistance to proteolytic degradation due to the polypeptide scaffold. A helix grafted protein of the disclosure comprises a C-peptide from a virus, such as HIV-1 gp41 C34 peptide, grafted onto a terminal helix of a polypeptide scaffold, such as a protein containing one or more Pleckstrin homology (PH) domain and/or PH-like domain. In particular, the helix grafted proteins provided herein are stable, helical and biologically active forms of the viral C-peptide which have enhanced resistance to proteolytic degradation (relative to that of the viral C-peptide that is not linked to the polypeptide scaffold). The helix grafted protein is generated in such a manner that the biological activity of the C-peptide (e.g., inhibition of viral infection of cells) is maintained and the structure of the scaffold is preserved.

I. Helix Grafted Protein

In an aspect, all or a portion of a C-peptide from a virus is grafted onto a terminal helix of a protein containing one or more Pleckstrin homology (PH) domain or PH-like domain. As used herein, "PH domain" is a protein domain of approximately 120 amino acids that occurs in a wide range of proteins involved in intracellular signaling or as constituents of cytoskeleton. The PH domains have a common structure consisting of two perpendicular antiparallel beta sheets, followed by a C-terminal amphipathic helix. A PH-like domain may be a phosphotyrosine-binding (PTB) domain. As used herein, "PTB domain", also referred to as phosphotyrosine-interaction domain or PI domain, is a protein domain which binds to phosphotyrosine. PTB domains are very similar to PH domains, but contain an extra α-helix in their structure. The PTB domain has a compact, 7-stranded beta-sandwich structure, capped by a C-terminal helix. Non-limiting examples of proteins containing a PH domain include the following families: Pleckstrin; Ser/Thr protein kinases such as Akt/Rac family, the beta-adrenergic receptor kinases, the mu isoform of PKC and the trypanosomal NrkA family; Tyrosine protein kinases belonging to the Btk/Itk/Tec subfamily; Insulin Receptor Substrate 1 (IRS-1); regulators of small G-proteins such as guanine nucleotide releasing factor GNRP (RasGRF), guanine nucleotide exchange proteins such as vav, dbl, SoS and *S. cerevisiae* CDC24, GTPase activating proteins such as rasGAP and BEM2/IPL2, and the human break point cluster protein bcr; cytoskeletal proteins such as dynamin, *Caenorhabditis elegans* kinesin-like protein unc-104, spectrin beta-chain, syntrophin, and *S. cerevisiae* nuclear migration protein NUM1; mammalian phosphatidylinositol-specific phospholipase C (PI-PLC) isoforms gamma and delta; Oxysterol-binding proteins OSBP, *S. cerevisiae* OSH1 and YHR073w; mouse protein citron; several *S. cerevisiae* proteins involved in cell cycle regulation and bud formation such as BEM2, BEM3, BUD4 and the BEM1-binding proteins BOI2 (BEB1) and BOI1 (BOB1); *C. elegans* protein MIG-10; and ceramide kinase. Non-limiting examples of human genes encoding proteins containing a PH domain include: ABR, ADRBK1, ADRBK2, AFAP, AFAP1, AFAP1L1, AFAP1L2, AKAP13, AKT1, AKT2, AKT3, ANLN, APBBlIP, APPL1, APPL2, ARHGAP10,ARHGAP12, ARHGAP15, ARHGAP21, ARHGAP22, ARHGAP23, ARHGAP24, ARHGAP25, ARHGAP26, ARHGAP27, ARHGAP9, ARHGEF16, ARHGEF18, ARHGEF19, ARHGEF2, ARHGEF3, ARHGEF4, ARHGEF5, ARHGEF6, ARHGEF7, ARHGEF9, ASEF2, BMX, BTK, C20orf42, C9orf100, CADPS, CADPS2, CDC42BPA, CDC42BPB, CDC42BPG, CENTA1, CENTA2, CENTB1, CENTB2, CENTB5, CENTD1, CENTD2, CENTD3, CENTG1, CENTG2, CENTG3, CIT, CNKSR1, CNKSR2, COL4A3BP, CTGLF1, CTGLF2, CTGLF3, *CTGLF4, CTGLF5, CTGLF6, DAB2IP, DAPP1, DDEF1, DDEF2, DDEFL1, DEF6, DEPDC2, DGKD, DGKH, DGKK, DNM1, DNM2, DNM3, DOCK10, DOCK11, DOCK9, DOK1, DOK2, DOK3, DOK4, DOK5, DOK6, DTGCU2, EXOC8, FAM109A, FAM109B, FARP1, FARP2, FGD1, FGD2, FGD3, FGD4, FGD5, FGD6, GAB1, GAB2, GAB3, GAB4, GRB10, GRB14, GRB7, IRS1, IRS2, IRS4, ITK, ITSN1, ITSN2, KALRN, KIF1A, KIF1B, KIF1Bbeta, MCF2, MCF2L, MCF2L2, MRIP, MYO10, NET1, NGEF, OBPH1, OBSCN, OPHN1, OSBP, OSBP2, OSBPL10, OSBPL11, OSBPL3, OSBPL5, OSBPL6, OSBPL7, OSBPL8, OSBPL9, PHLDA2, PHLDA3, PHLDB1, PHLDB2, PHLPP, PIP3-E, PLCD1, PLCD4, PLCG1, PLCG2, PLCH1, PLCH2, PLCL1, PLCL2, PLD1, PLD2, PLEK, PLEK2, PLEKHA1, PLEKHA2, PLEKHA3, PLEKHA4, PLEKHA5, PLEKHA6, PLEKHA7, PLEKHA8, PLEKHB1, PLEKHB2, PLEKHC1, PLEKHF1, PLEKHF2, PLEKHG1, PLEKHG2, PLEKHG3, PLEKHG4, PLEKHG5, PLEKHG6, PLEKHH1, PLEKHH2, PLEKHH3, PLEKHJ1, PLEKHK1, PLEKHM1, PLEKHM2, PLEKHO1, PLEKHQ1, PREX1, PRKCN, PRKD1, PRKD2, PRKD3, PSCD1, PSCD2, PSCD3, PSCD4, PSD, PSD2, PSD3, PSD4, RALGPS1, RALGPS2, RAPH1, RASA1, RASA2, RASA3, RASA4, RASAL1, RASGRF1, RGNEF, ROCK1, ROCK2, RTKN, SBF1, SBF2, SCAP2, SGEF, SH2B, SH2B1, SH2B2, SH2B3, SH3BP2, SKAP1, SKAP2, SNTA1, SNTB1, SNTB2, SOS1, SOS2, SPATA13, SPNB4, SPTBN1, SPTBN2, SPTBN4, SPTBN5, STAP1, SWAP70, SYNGAP1, TBC1D2, TEC, TIAM1, TRIO, TRIOBP, TYL, URP1, URP2, VAV1, VAV2, VAV3, and VEPH1. Non-limiting examples of human genes encoding proteins containing a PTB domain include: APBA1, APBA2, APBA3, EPS8, EPS8L1, EPS8L2, EPS8L3, TENC1, TNS, TNS1, TNS3, TNS4, DOK1, DOK2, DOK3, DOK4, DOK5, DOK6, DOK7, FRS2, FRS3, IRS1, IRS2, IRS4, TLN1, and TLN2.

Additional proteins with PH domains and/or PH-like domains may be identified via methods standard in the art. For example, protein structure prediction may be determined by various databases, such as Phyre and Phyre2. Such databases generate reliable protein models that may be used to determine structural homologs. The main results table in Phyre2 provides confidence estimates, images and links to the three-dimensional predicted models and information derived from either Structural Classification of Proteins database (SCOP) or the Protein Data Bank (PDB) depending on the source of the detected template. For each match a link takes the user to a detailed view of the alignment between the user sequence and the sequence of known three-dimensional structure. See www.sbg.bio.ic.ac.uk/phyre2/ for more details. Preferably, the PH domain and/or PH-like domain containing protein is expressible in *E. coli*, soluble and endogenous to humans or mammals. Protein expression and solubility may be confirmed via methods known in the art such as a protein gel and/or absorbance assays.

A protein containing one or more PH and/or PH-like domain may be mutated (i.e. not the natural form found in nature) to disrupt its native function. It is known in the art that the native function of PH domains can be turned off by a single mutation via site directed mutagenesis.

Proteins containing PH and PH-like domains for use herein are generally ≤20 kDa and comprise a C-terminal and/or N-terminal, solvent exposed helix. The helix may be of varying lengths from about 10 to about 40 amino acid residues. Accordingly, the helix may be about 15 to about 35 residues, or about 15 to about 30 residues, or about 15 to about 25 residues, or about 15 to about 20 residues. For example, the helix may be about 17, about 18, about 19, about 20, about 21, about 22, about 23, about 24, about 25, about 26, about 27, about 28, about 29 or about 30 residues. Additionally, the helicity (percent of helical residues relative to total residues) may be of varying amounts from about 10% to about 30%. Accordingly, the helicity may be about 10% to about 25%, or about 10% to about 20%, or about 10% to about 15%. For example, the helicity may be about 12%, about 13%, about 14%, about 15%, about 16%, about 17%, about 18%, about 19%, about 20%, about 21%, about 22%, about 23%, about 24%, or about 25%. It may also be beneficial for the protein containing one or more PH and/or PH-like domain to comprise disulfide bonds to help stabilize the tertiary structure of the protein.

A protein containing one or more PH domain and/or PH-like domain is selected from the group consisting of GLUE, HOMER, PLECKSTRIN, PKB, AKT2, DYNAMIN, APPL1-PTB, APPL1-PH, DOK5, and ELMO. Alternatively, a protein containing one or more PH domain and/or PH-like domain is selected from the group consisting of GLUE, HOMER, PLECKSTRIN, AKT2, DOK5, and jELMO. In one embodiment, a protein containing one or more PH domain and/or PH-like domain is GLUE (GRAM-Like Ubiquitin-binding in EAP45). In another embodiment, a protein containing one or more PH domain and/or PH-like domain is ELMO (Engulfment and Cell Motility).

As mentioned above, a protein containing one or more PH domain and/or PH-like domain comprises a C-terminal or N-terminal, solvent exposed α-helix, also referred to herein as a "terminal helix". The terminal helix is then altered such that all or a portion of a C-peptide from a virus is grafted onto the terminal helix. If the protein containing one or more PH domain and/or PH-like domain is GLUE, then the terminal helix comprises SEQ ID NO:1 (GVLFSQATER-ALENILT). If the protein containing one or more PH domain and/or PH-like domain is ELMO, then the terminal helix comprises SEQ ID NO:5 (PILELKEKIQPEILE-LIKQQRLNRLVE) or SEQ ID NO:6 (DKHEYCIWTDG-LNALLGK). Methods standard in the art may be used to determine the sequence and structure of a terminal helix of a protein containing one or more PH domain and/or PH-like domain.

To graft all or a portion of a C-peptide from a virus onto a terminal helix, the structure of the terminal helix of the protein containing one or more PH domain and/or PH-like domain is aligned with the structure of a C-peptide from a virus. Accordingly, the structure of the terminal helix and the structure of the C-peptide are overlaid. Numerous methods are available to overlay structures such as SWISS_MODEL, PyMOL, Modeller, Chimera, Phyre, TMalign, Coot, VAST, DALI. For example, PyMOL pair_fit algorithm may be used to overlay the two helical structures. Once the helical structures have been overlaid, amino acid residues, also referred to herein as "residues", on the terminal helix of the protein containing one or more PH domain and/or PH-like domain may be selected for mutation. Specifically, residues on the terminal helix of the protein containing one or more PH domain and/or PH-like domain may be mutated to residues of a C-peptide from a virus. Alternatively, the terminal helix of the protein containing one or more PH domain and/or PH-like domain may be extended using residues of a C-peptide from a virus. Further, the terminal helix of the protein containing one or more PH domain and/or PH-like domain may be truncated and then extended using residues of a C-peptide from a virus. Still further, residues on the terminal helix of the protein containing one or more PH domain and/or PH-like domain may be mutated to residues of a C-peptide from a virus and, also, the terminal helix may be extended using residues of the C-peptide. Additionally, residues on the terminal helix of the protein containing one or more PH domain and/or PH-like domain may be mutated to residues of a C-peptide from a virus and, also, the terminal helix may be truncated and then extended using residues of the C-peptide.

When selecting residues for mutation on the terminal helix of the protein containing one or more PH domain and/or PH-like domain, it is preferable to maintain the residues oriented toward the interior of the helix and alter only those residues that are solvent exposed. Without wishing to be bound by theory, the interior residues are crucial for the protein structure, whereas the solvent exposed, or exterior residues, are not crucial to the protein structure. Preferably, the solvent exposed residues of the terminal helix are mutated to the critical binding residues of a C-peptide from a virus. This must be done in such a way as to roughly preserve the three-dimensional conformation of the residues at the binding interface. It is within the skill of one in the art to identify residues on the C-peptide that are critical for binding. One or more residues of the terminal helix may be mutated to residues of the C-peptide. Ultimately, each solvent exposed residue of the terminal helix may be mutated to residues of the C-peptide. For example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more or 20 or more residues of the terminal helix may be mutated to residues of the C-peptide. Accordingly, 1, 2, 3, 4, 5, 6, 7, 8, 9, 10, 11, 12, 13, 14, 15, 16, 17, 18, 19 or 20 residues of the terminal helix may be mutated to residues of the C-peptide. Alternatively, about 5 to about 10 residues of the terminal helix may be mutated to residues of the C-peptide. Optionally, zero residues of the terminal helix are mutated and one or more residues of the C-peptide are used to extend the terminal helix. Alternatively, one or more residues of the terminal helix are mutated and one or more residues of the C-peptide are used to extend the terminal helix. For example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, or 35 or more residues of the C-peptide are used to extend the terminal helix. Accordingly, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 residues of the C-peptide are used to extend the terminal helix. Prior to extending the terminal helix with residues of a C-peptide, the terminal helix may be truncated. For example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more or 20 or more residues may be truncated from the terminal helix. Accordingly, 1, 2, 3, 4, 5, 6, 7, 8, 9, 10, 11, 12, 13, 14, 15, 16, 17, 18, 19 or 20 residues may be truncated from the terminal helix.

As used herein, a "C-peptide" is a stable helical structure derived from a virus. However, it is understood that the methods disclosed herein may be applied to other stable helical structures that are not virus derived. Certain viruses comprise a transmembrane unit which contains several regions that are responsible for the merge of the viral membrane and the target cell membrane. A first region of the transmembrane unit is a fusion peptide which is important for inducing viral entry, promoted by anchoring itself into the host membrane. A second region and third region are C-terminal heptad repeats (CHR; also referred to herein as CHR peptides or C-peptides) and N-terminal heptad repeats (NHR). NHR self-interacts forming a central trimeric coiled-coil with three large hydrophobic pockets. Three helical CHR peptides are able to bind the trimeric NHR structure in an antiparallel fashion. The resulting structure is referred to as a 6-helix bundle (6HB) and is important for viral infection. See, for example FIG. 9. As such, a C-peptide of the disclosure binds to a NHR. A C-peptide may also bind to a fusion peptide. A C-peptide may be from any virus known to form a 6HB or categorized into the structurally defined "class I" viral membrane fusion glycoproteins. Non-limiting examples of viruses known to form a 6HB or categorized into class I envelope glycoproteins include retroviruses, orthoviruses, paramyxoviruses and filoviruses. For example, human immunodeficiency virus (HIV), simian immunodeficiency virus (SIV), severe acute respiratory syndrome coronavirus (SARS), parainfluenza virus (SV5), Hendra/Nipah paramyxoviruses, Ebola virus (EboV), Marburg virus (MarV), influenza virus, Newcastle disease virus, mumps virus, and respiratory syncytial virus are known to form a 6HB or categorized into class I envelope glycoproteins. A skilled artisan would be able to identify C-peptides found in a virus. In an embodiment, a C-peptide is from HIV. More specifically, a C-peptide is from HIV gp41. Even more specifically, a C-peptide is SEQ ID NO:2 (WMEWDREINNYTSLIHSLIEESQNQQEKNEQELL), also known in the art as C34.

It is not necessary that the entire C-peptide is used. A portion that includes an appropriate amino acid composition (number and identity of amino acid residues) such that it retains function (e.g., binding to a NHR or fusion peptide such that it is an inhibitor of viral infection) may be grafted onto a protein containing one or more PH domain and/or PH-like domain. For example, all or a portion of a C-peptide, such as all or a portion of gp41 C34, may be used. Accordingly, a C-peptide from a virus may be 10 or more residues. For example, a C-peptide from a virus may be 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, or 50 or more residues. Accordingly, a C-peptide from a virus may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 residues. Specifically, a C-peptide from a virus may be about 15 to about 40 residues.

As mentioned above, all or a portion of a C-peptide from a virus is grafted onto a terminal helix of a protein containing one or more PH domain and/or PH-like domain. Exemplified herein is all or a portion of C34 C-peptide grafted onto a terminal helix of GLUE, ELMO, HOMER, PLECKSTRIN, AKT2 and DOK5. In an embodiment, the protein containing one or more PH domain and/or PH-like domain is GLUE and the C-peptide grafted onto the terminal helix of GLUE comprises SEQ ID NO:3 (GVWFSWATEIALYTILIHSLIEESQNQQEKNEQELL). In another embodiment, the protein containing one or more PH domain and/or PH-like domain is ELMO and the C-peptide grafted onto the N-terminal helix of ELMO comprises SEQ ID NO:7 (WMEWDREINNYTSLIHSLIEESQNQQKQQRLNRLVE). In still another embodiment, the protein containing one or more PH domain and/or PH-like domain is ELMO and the C-peptide grafted onto the C-terminal helix of ELMO comprises SEQ ID NO:8 (DKWEYWIWTIGLYTLLGKSLIEESQNQQEKNEQELL).

A C-peptide and/or protein containing one or more PH domain and/or PH-like domain may be obtained from natural sources (purified, partially purified), recombinantly produced, chemically synthesized or obtained from commercial sources. A helix grafted protein may comprise naturally occurring amino acids, synthetic amino acids, genetically encoded amino acids, non-genetically encoded amino acids, and combinations thereof. A helix grafted protein may include both L-form and D-form amino acids. Representative non-genetically encoded amino acids may include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmo sine; allo-isoleucine; N-methylglycine (sarcosine); N-methylisoleucine; N-methylvaline; norvaline; norleucine; and ornithine. Representative derivatized amino acids may include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

The term "conservatively substituted variant" refers to a helix grafted protein comprising an amino acid residue sequence similar to a sequence of a reference protein containing one or more PH domain and/or PH-like domain in which one or more residues have been conservatively substituted with a functionally similar residue and which displays the activity as described herein. The phrase "conservatively substituted variant" also includes a helix grafted protein wherein a residue is replaced with a chemically derivatized residue, provided that the resulting helix grafted protein displays activity as disclosed herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

A helix grafted protein of the disclosure maintains a similar overall protein structure as compared to the protein containing one or more PH domain and/or PH-like domain. As such, grafting the C-peptide onto the terminal helix of the protein containing one or more PH domain and/or PH-like domain does not drastically alter the folding of the ungrafted protein containing one or more PH domain and/or PH-like domain. Methods of determining protein structure are known in the art. For example, circular dichroism (CD) may be used to detect macroscopic structural changes. A helix grafted protein may have a similar overall protein structure compared to the protein containing one or more PH domain and/or PH-like domain as measured my CD. Alternatively, a helix grafted protein may have enhanced helicity compared to the protein containing one or more PH domain and/or PH-like domain as measured my CD.

Further, a helix grafted protein of the disclosure displays improved stability relative to the ungrafted C-peptide. For example, a helix grafted protein of the disclosure may display improved serum stability relative to the ungrafted C-peptide. To determine serum stability, a helix grafted protein may be incubated with serum, such as human serum, and the amount of protein may be measured at various times following incubation. Methods of measuring amount of protein are standard in the art. For example, absorbance may be measured and/or SDS-PAGE gels and immunoblots may be used. A helix grafted protein of the disclosure may remain stable for more than 1 hour following incubation with serum. For example, a helix grafted protein of the disclosure may remain stable for more than 1, more than 2, more than 3, more than 4, more than 5, more than 6, more than 7, more than 8, more than 9, more than 10, more than 11, more than 12, more than 16, more than 24 hours, more than 36, more than 48, more than 60, more than 72, more than 84, more than 96, more than 108, or more than 120 hours. Additionally, a helix grafted protein of the disclosure may display improved thermal stability relative to the ungrafted C-peptide. Methods of measuring thermal stability are standard in the art. For example, protein structure may be measured as the protein is subjected to increasing amounts of heat. A helix grafted protein of the disclosure may remain stable at temperatures of greater than 60° C. For example, a helix grafted protein of the disclosure may remain stable at temperatures of greater than 60° C., greater than 65° C., greater than 70° C., greater than 75° C., greater than 80° C., or greater than 85° C.

Importantly, a helix grafted protein of the disclosure binds via its grafted terminal helix to the cognate binding partner of the C-peptide. As used herein, "cognate binding partner", is the molecule that typically interacts with the C-peptide. For example, a helix grafted protein comprising a grafted C-peptide binds to the same binding partner as the C-peptide that was used to graft onto the terminal helix of the protein containing one or more Pleckstrin homology (PH) domain and/or PH-like domain. Methods of measuring binding or protein-protein interactions are known in the art and detailed in the examples. A helix grafted protein may bind to the cognate binding partner of the C-peptide the same or better than the ungrafted C-peptide. Or, a helix grafted protein maybe bind to the cognate binding partner of the C-peptide slightly less than the ungrafted C-peptide. As there are many ways to measure binding, the difference in binding may be indicated as a ratio or p-value. For example, a helix grafted protein binds to the cognate binding partner of the C-peptide the same or better than the ungrafted C-peptide if the ratio of the binding of the helix grafted protein as compared with the binding of the ungrafted C-peptide is greater than or equal to 1.0. For example, a ratio of greater than 1, 1.2, 1.5, 1.7, 2, 3, 3, 5, 10, 15, 20 or more. In another embodiment, the increase or decrease in binding is measured using p-value. For instance, when using p-value, a helix grafted protein is identified as binding to the cognate binding partner of the C-peptide the same or better than the ungrafted C-peptide when the p-value is less than 0.1, preferably less than 0.05, more preferably less than 0.01, even more preferably less than 0.005, the most preferably less than 0.001. If there is a decrease in binding of the helix grafted protein relative to the ungrafted C-peptide, then preferably the p-value is greater than 0.05. However, a p-value of less than 0.05 may be acceptable if viral infection is still inhibited. By slightly less is meant that the helix grafted protein binds to the cognate binding partner of the C-peptide relative to the ungrafted C-peptide at a ratio of less than 1 but still inhibits viral infection. Viral infection may be measured via methods standard in the art or as detailed in the Examples.

(a) Pharmaceutical Compositions

The disclosure also provides pharmaceutical compositions. The pharmaceutical composition comprises a helix grafted protein, as the active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulo se, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally (including inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

Controlled or time release (gradual release, release at a particular time after administration or insertion) of the helix grafted protein can be effected by, for example, incorporating the helix grafted protein into a composition which releases the helix grafted protein gradually or after a defined period of time. Alternatively, the helix grafted protein can be incorporated into a composition which releases the helix grafted protein immediately or soon after its administration or application (e.g., into the vagina, mouth or rectum). Combined release (e.g., release of some of the helix grafted protein immediately or soon after insertion, and over time or at a particular time after insertion) can also be effective (e.g., by producing a composition which is comprised of two or more materials: one from which release or delivery occurs immediately or soon after insertion and/or one from which release or delivery is gradual and/or one from which release occurs after a specified period). For example, a helix grafted protein can be incorporated into a sustained release composition such as that taught in U.S. Pat. No. 4,707,362. The cream, foam, gel or suppository can be one also used for birth control purposes (e.g., containing a spermicide or other contraceptive agent), although that is not necessary (e.g., it can be used solely to deliver the helix grafted protein, alone or in combination with another non-contraceptive agent, such as an antibacterial or antifungal drug or a lubricating agent).

In certain embodiments, a helix grafted protein is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a helix grafted protein in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, a helix grafted protein may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9,12,15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a helix grafted protein (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. A helix grafted protein may be encapsulated in a microemulsion by any method generally known in the art.

In yet another embodiment, a helix grafted protein may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Methods

In an aspect, the disclosure provides a method of inhibiting entry of virus into cells of a subject. The method comprises administering to the subject a composition comprising a helix grafted protein comprising all or a portion of a C-peptide from a virus grafted onto a terminal helix of a protein containing one or more Pleckstrin homology (PH) domain and/or PH-like domain. The helix grafted protein may be administered to an uninfected subject or an infected subject. Inhibition of viral entry into cells has been shown to inhibit viral infection. Accordingly, the disclosure also provides a method of treating or preventing viral infection in a subject. The method comprises administering to the subject a composition comprising a helix grafted protein comprising all or a portion of a C-peptide from a virus grafted onto a terminal helix of a protein containing one or more Pleckstrin homology (PH) domain and/or PH-like domain. As used herein, "preventing" viral infection may also refer to "protecting" from viral infection and refers to prophylactic use.

In another aspect, the disclosure provides a method to reduce the amount of virus in a subject infected with a virus. The method comprises administering to the subject a composition comprising a helix grafted protein comprising all or a portion of a C-peptide from a virus grafted onto a terminal helix of a protein containing one or more Pleckstrin homology (PH) domain and/or PH-like domain.

A virus may be a virus known to form a 6HB or categorized into the structurally defined "class I" viral membrane fusion glycoproteins. Non-limiting examples of viruses known to form a 6HB or categorized into class I envelope glycoproteins include retroviruses, orthoviruses, paramyxoviruses and filoviruses. For example, human immunodeficiency virus (HIV), simian immunodeficiency virus (SIV), severe acute respiratory syndrome coronavirus (SARS), parainfluenza virus (SV5), Hendra/Nipah paramyxoviruses, Ebola virus (EboV), Marburg virus (MarV), influenza virus, Newcastle disease virus, mumps virus, and respiratory syncytial virus are known to form a 6HB or categorized into class I envelope glycoproteins. Specifically, a virus may be HIV.

As used herein, the terms "viral infection", "infection by a virus", and the like, refer to the ability of a virus to carry out all steps in the viral life cycle, resulting in the production of infectious particles. Such a life cycle comprises a variety of steps including, for example, attachment, uncoating, transcription, translation, protein processing, replication of nucleic acid molecules, assembly of viral particles, intracellular transport of viral particles, budding, release and the like. Other steps may also be included depending on the virus.

As used herein, the terms "inhibit viral infection", "inhibit infection by a virus", "inhibit entry of virus", "treat viral infection", and the like, refer to decreasing the amount of virus present in an infected cell or subject relative to the amount of virus present in a cell or subject that has not been administered a helix grafted protein. Also encompassed is the ability to prevent viral infection. Inhibition of viral infection can be effected in a patient infected with a virus, or it can be effected in cells in culture (e.g., tissue culture). It should be appreciated that the terms amount and concentration can be used interchangeably. An amount of virus can also be referred to as a titer. It is also understood by those of skill in the art that the amount of virus can refer to the total number of viral particles, or it can refer to the number of viral particles that are infectious, i.e. capable of carrying out the viral life cycle, including the ability to effect another cycle of infectious particle formation. For example, in a given population of virus particles, some or all of the particles may be unable to carry out a specific step in its life cycle (e.g., attachment or entry) due to a deficiency in a molecule needed to perform that step. While the number of particles in the population may be large, the number of infectious particles could be small to none. Thus the amount of virus determined by counting virus particles may differ from that determined by measuring functional virus in, for example, a plaque assay. Accordingly methods of the disclosure can affect the total number of viral particles produced, as well as the number of infectious viral particles produced. Appropriate methods of determining the amount of virus are understood by those skilled in the art and include, but are not limited to, directly counting virus particles, titering virus in cell culture e.g., plaque assay), measuring the amount of viral protein(s), measuring the amount of viral nucleic acids, or measuring the amount of a reporter protein, e.g., luciferase, GFP.

Inhibition of viral infection can result in a partial reduction in the amount of virus, or it can result in complete elimination of virus from a cell or subject or in prevention of viral infection. The amount of virus is reduced by at least 5%, at least 10%, at least 20%, at least 30%, at least 40%, at least 50%, at least 60%, at least 70%, at least 80%, at least 90%, or at least 95%. Alternatively, the amount of virus is reduced by a factor of at least 10, at least 50, at least 100, at least 500, at least 1000, at least 5000, or at least 10,000. In one embodiment, the viral infection is completely inhibited (i.e., there are no infectious particles).

The composition is described in Section I, the subject and administration are described in more detail below.

(a) Subject

A method of the disclosure may be used to treat or prevent viral infection in a subject that is a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In certain embodiments, the animal is a laboratory animal. Non-limiting examples of a laboratory animal may include rodents, canines, felines, and non-human primates. In other embodiments, the animal is a rodent. Non-limiting examples of rodents may include mice, rats, guinea pigs, etc. In a specific embodiment, the subject is a human.

(b) Administration

In certain aspects, a therapeutically effective amount of a composition of the invention may be administered to a subject. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. For example, a helix grafted protein may be included in a composition which is applied to or contacted with a mucosal surface, such as the vaginal, rectal or oral mucosa. Local administration, including directly into the central nervous system (CNS) includes but is not limited to via a lumbar, intraventricular or intraparenchymal catheter or using a surgically implanted controlled release formulation. The route of administration may be dictated by the disease or condition to be treated. It is within the skill of one in the art, to determine the route of administration based on the disease or condition to be treated. Alternatively, blood or bone marrow may be removed from a subject infected with or thought to be infected with a virus, treated with (combined with) a helix grafted protein of the disclosure and returned to the individual.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the peptides useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

A helix grafted protein of the disclosure can also be administered to a subject through the use of a contraceptive device (e.g., condom, cervical cap, diaphragm) which is coated with or has incorporated therein in a manner which permits release under conditions of use. Release of the helix grafted protein can occur immediately, gradually or at a specified time, as described above. As a result, they make contact with and bind virus and reduce or prevent viral entry into cells. In another embodiment, a helix grafted protein is administered or applied to a mucosal surface.

For therapeutic applications, a therapeutically effective amount of a composition of the invention is administered to a subject. A "therapeutically effective amount" is an amount of the therapeutic composition sufficient to produce a measurable response (e.g., a reduction in infection, reduction in viral particles, reduction in symptoms associated with viral infection). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, the virus, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. In certain embodiments, a therapeutically effective amount may be 100 nM or more of a helix grafted protein. For example, a therapeutically effective amount may be about 100 nM, about 250 nM, about 500 nM, about 750 nM, about 1 µM, about 10 µM, about 100 µM, about 1 mM, about 10 mM, or about 100 mM or more.

The timing of administration of the treatment relative to the disease itself and duration of treatment will be determined by the circumstances surrounding the case. Treatment could begin in a hospital or clinic itself, or at a later time after discharge from the hospital or after being seen in an outpatient clinic.

Duration of treatment could range from a single dose administered on a one-time basis to a life-long course of therapeutic treatments. The duration of treatment can and will vary depending on the subject and the disease or disorder to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The frequency of dosing may be once, twice, three times or more daily or once, twice, three times or more per week or per month, or as needed as to effectively treat the symptoms or disease. In certain embodiments, the frequency of dosing may be once, twice or three times daily. For example, a dose may be administered every 24 hours, every 12 hours, or every 8 hours. In other embodiments, the frequency of dosing may be once, twice or three times weekly. For example, a dose may be administered every 2 days, every 3 days or every 4 days. In a different embodiment, the frequency of dosing may be one, twice, three or four times monthly. For example, a dose may be administered every 1 week, every 2 weeks, every 3 weeks or every 4 weeks.

A helix grafted protein of the disclosure, or a composition thereof, may be administered alone or in combination with one or more other pharmaceutical agents, including other compounds of the present invention.

Although the foregoing methods appear the most convenient and most appropriate and effective for administration of a composition of the invention, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

GLUE that Sticks to HIV: a Helix-Grafted GLUE Protein that Selectively Binds the HIV gp41 N-Terminal Helical Region The ongoing discovery of new drug therapies is of vital importance to human health. The traditional pharmaceutical paradigm for this discovery centers on small molecules binding to well-defined protein pockets, typified by enzyme active sites. However, there remain countless important targets largely beyond the reach of this strategy, principally due to extended contact surfaces. Such interactions are often collected under the heading of "protein—protein interactions" or PPIs.

A medicinally significant subset of these PPIs feature binding of one protein to an exposed helix on another, which has sparked considerable interest in the synthetic replication of helical epitopes as a route to novel therapeutics. Various strategies have been employed, including oligomeric organic scaffolds that project side chains along appropriate vectors, covalently constrained (or "stapled") peptides, and helical "foldamers" employing natural or unnatural backbone architectures. Each has produced effective agents, but all require non-trivial synthetic effort and expense.

A more accessible suite of ligands might be had by exploiting the flexibility and feasibility of protein expression. If one could identify a scaffold protein bearing a helix with at least one solvent-exposed face, and if that protein was simple and stable enough to facilitate easy expression and tolerate varying the exposed helical residues and helix length, it could serve as a generic canvas upon which to paint any desired helical interface. The result would be a "protein graft" in which residues critical to recognition of a particular epitope are grafted onto the host protein in appropriate positions. The general concept of grafting is an established method for mimicking protein surfaces.

Herein is reported a successful application of a specific "helix-grafting" technique to a PPI crucial for HIV infection. The HIV fusion protein gp41 operates in part by binding a C-terminal helix (C-peptide) onto a trimeric N-terminal coiled coil. It is shown herein that grafting of gp41 C-peptide residues onto the exposed helical face of a suitable host affords a new ligand that expresses well in *Escherichia coli*, exhibits excellent serum stability, and is capable of replicating the native interaction.

Figure 1A:
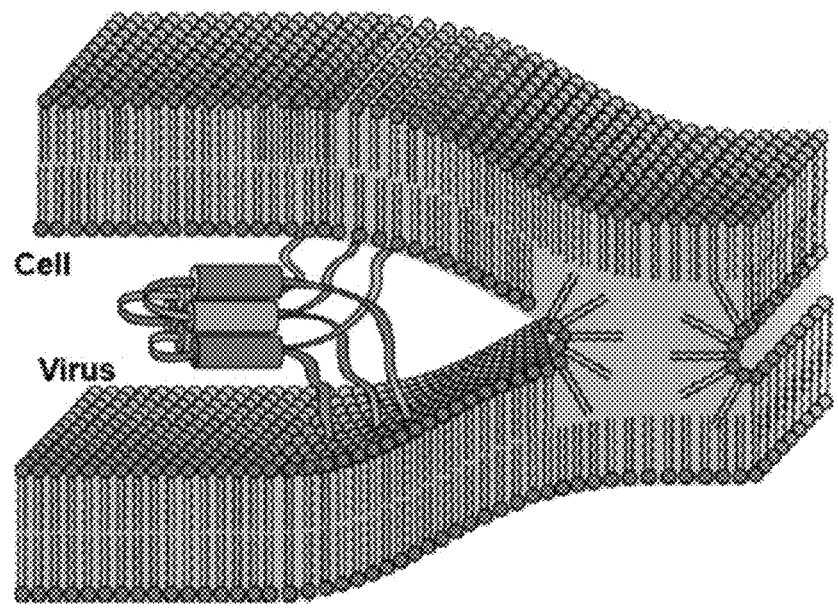
Figure 1B:
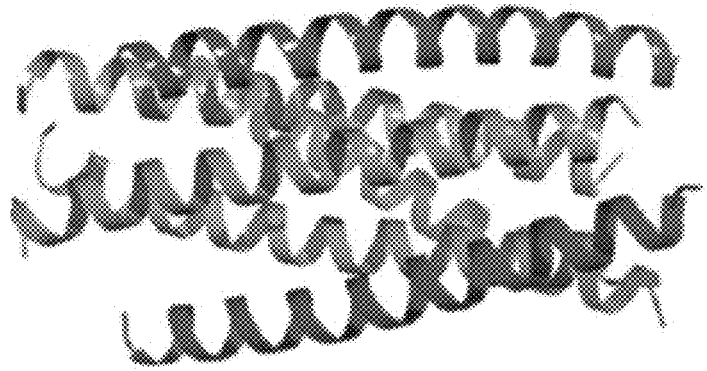

Following initial attachment to a target cell, HIV entry is effected by fusion of the respective cell membranes, mediated by gp41. In the prefusogenic state, gp41 is trimerized via an N-terminal heptad repeat (NHR), and an N-terminal fusion peptide inserts into the target membrane. The protein then undergoes a conformational rearrangement in which the C-peptide packs as an antiparallel helix against the surface of the NHR trimer. Anchoring of the respective protein termini into viral and cell membranes ensures that this rearrangement requires membrane juxtaposition and thus provides a mechanism for promoting fusion (FIG. 1). Peptides derived from this C-peptide helix (some as short as 12-16 residues) have been shown to bind the coiled coil and inhibit membrane fusion by HIV in human cells. The best known of these, enfuvirtide (marketed as Fuzeon), consists of 36 residues and is an FDA-approved treatment. However, like other short peptide drugs, its chemical synthesis is extraordinarily expensive and it exhibits poor serum stability ($t_{1/2}$ ~3.8 h). It was reasoned that a helix-grafted alternative might retain similar specificity but have improved stability, solubility, and availability.

In designing the first-generation helix-grafted protein, a Pleckstrin homology (PH) domain called GLUE (GRAM-LikeUbiquitin-binding in EAP45, FIG. 2A, gray), which is derived from a subunit of the endosomal sorting complex, was used. Like other members of the PH family, the GLUE domain contains a C-terminal amphipathic helix resting in a cleft formed by two opposing β-sheets, with one face presented to solvent. This relatively rare arrangement is well suited to serve as a helix grafting scaffold. Although the native GLUE helix is only 16 residues, known structures of other PH domains with helices up to 29 residues suggested that it could be extended to a length comparable to the C-peptide without structural compromise. In addition to its well-positioned helix platform, GLUE is a relatively small (~15 kDa) and stable protein. Finally, native GLUE function relies on an affinity for phospholipids that can be abolished by a single Arg107Ala mutation, making it suitable for future intracellular targets without fear of disrupting lipid trafficking.

Figure 2A:
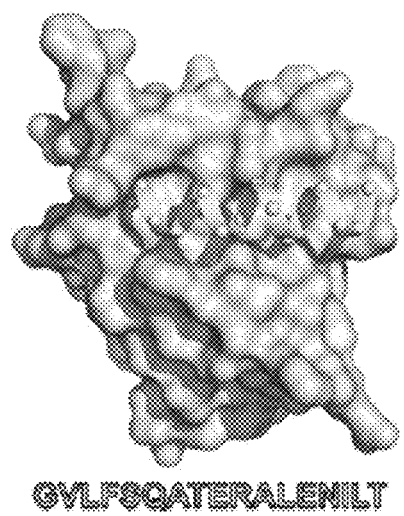
Figure 2B:
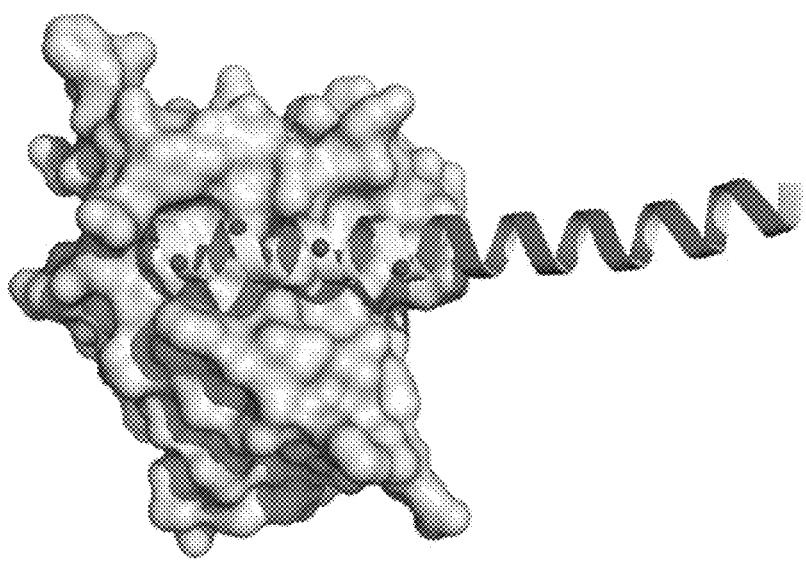

First, the native helix on GLUE (FIG. 2A, grey) was aligned with a single C-peptide helix from gp41 (FIG. 2A, purple). Backbone atoms from the GLUE helix (PDB ID: 2CAY) were aligned with the corresponding number from the N-terminal segment of the gp41 C-peptide (PDB ID: 1AIK) by using the PyMOL pair_fit algorithm. The overlay was very good (RMSD of 0.44 Å over 60 atoms), and allowed the confident selection of six positions on the GLUE helix at which side chains from the gp41 sequence could be installed in such a way as to replicate their native three-dimensional positions. The helix was then extended by attaching a pure gp41 sequence to the C terminus of GLUE (FIG. 2B), such that the total length of the new helix was appropriate for binding to the trimeric N-terminal coiled coil. The final sequence was expressed as a soluble protein in E. coli.

Figure 3A:
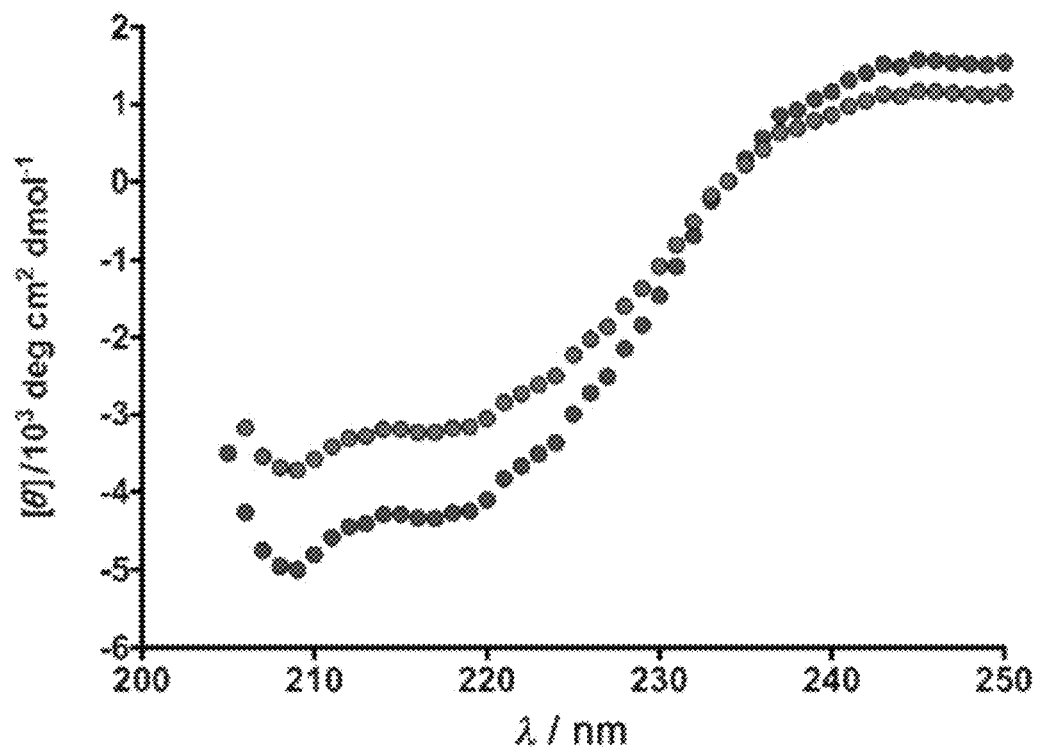
Figure 3B:
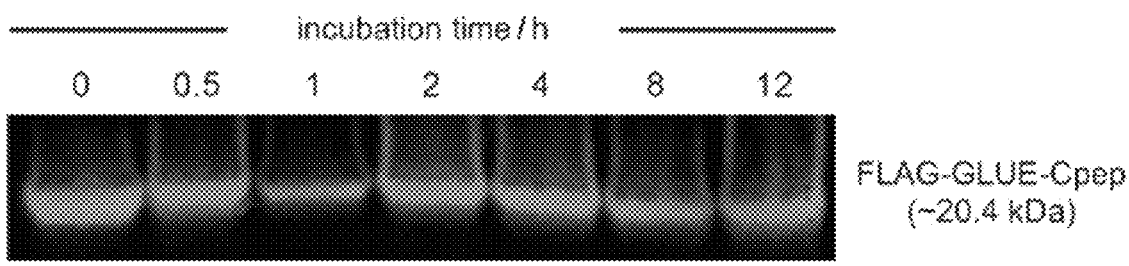

Both wild-type GLUE (wtGLUE) and the helix-grafted variant (referred to as GLUE-Cpep herein) were characterized by circular dichroism (CD) to probe for macroscopic structural changes (FIG. 3A). Both proteins display a similar overall signal, suggesting that the grafting process does not compromise the GLUE domain fold. As one element of the design was the expectation that a well-folded protein domain would exhibit improved serum stability compared to an isolated short peptide, a serum stability test using a standard assay was next conducted (H. Jenssen, S. I. Aspmo, *Meth. Mol. Biol.* 2008, 494, 177-186). FLAG-tagged GLUE-Cpep, incubated with human serum for up to 12 h, showed no appreciable degradation by western blot analysis (FIG. 3B). This supports a significant serum stability enhancement for the grafted protein compared to isolated peptides such as enfuvirtide.

Direct analysis of the binding interaction between GLUE-Cpep and the NHR receptor by simple mixing of the two components is complicated by several factors: proper self-assembly of the N-terminal peptide, the potential for one, two, or three GLUE-derived ligands per complex, and the known susceptibility of unbound N-peptide trimers to aggregation/precipitation. Fortunately, these challenges have long been recognized, and several solutions exist. A construct called 5-helix, based on initial work by Kim and co-workers, was used (M. J. Root, M. S. Kay, P. S. Kim, *Science* 2001, 291, 884-888). It solves the problem of multiple equilibria and binding sites by covalently tethering five of the six subunits with short Gly/Ser loops. Thus, a single polypeptide contains three copies of the NHR domain and two C-peptides, such that when folded, it features the coiled coil with two of its binding sides already occupied and just a single exposed interface (FIG. 4A). Throughout, 5-helix as a receptor to assess complex formation with GLUE-Cpep was used. Initial CD characterization of the GLUE-Cpep/5-helix complex demonstrates binding-induced gains in helicity and thermal stability. The wavelength spectrum (FIG. 4B) exhibits a notably deeper signal for the 1:1 mixture than for either component alone, and the corresponding melt data (FIG. 4C) reveal a dramatic increase in thermal stability, as evidenced by a significant shift of the overall melting curve, though the change in $T_m$ is more modest (observed $T_m$ values of ~77, ~79, and ~83° C. for 5-helix, GLUE-Cpep, and the complex, respectively). The melting transition for the 1:1 sample is also highly cooperative, further supporting a well-defined assembly.

Having validated the GLUE-Cpep/5-helix interaction, next its viability in more complex environments was probed. Binding in living cells (*E. coli*) was first assessed by split-superpositive green fluorescent protein (split-spGFP) reassembly, a technique recently reported (B. D. Blakeley, A. M. Chapman, B. R. McNaughton, *Mol. BioSyst.* 2012, 8, 2036-2040). *E. coli* were co-transformed with plasmids encoding 5-helix fused to the N-terminal half of spGFP (N-spGFP-5-helix) and one of two C-spGFP fusions: GLUE-Cpep or the gp41 C-peptide by itself. Interaction-dependent reassembly of GFP fragments (to generate a fluorescent signal) was measured by flow cytometry. Cells expressing either ligand construct are highly fluorescent, in contrast to a control with nothing fused to C-spGFP (FIG. 4D). This interaction was further characterized by using ELISA. The grafted GLUE bound 5-helix with slightly better affinity than the native C-peptide (FIG. 4E, columns 3 and 4, respectively), whereas the wild-type GLUE exhibits no appreciable affinity (FIG. 4E, column 2), thus confirming the need for the grafted domain. This ELISA signal was observed even for a GLUE-Cpep sample that was pre-incubated with human serum (Supporting Information), confirming that the degradation-resistant form of the protein remains functional. Together, these experiments show that the helix-grafted GLUE binds 5-helix in the context of a complex cellular milieu, in a manner comparable to the native ligand and with improved serum longevity.

Binding selectivity was assessed by measuring the amount of protein that was copurified from *E. coli* expressing an untagged GLUE-Cpep(~17.1 kDa) and $His_6$-tagged 5-helix (ca. 25.4 kDa). As seen in FIG. 4F, the tagged 5-helix copurified with a single protein, which was identified as GLUE-Cpep by mass spectrometry (FIG. 6). The similar amounts of each copurified protein, as determined by densitometry measurements of each protein band, further indicated that the complex involved a 1:1 ratio of proteins. The relatively miniscule levels of other copurified cellular proteins indicates excellent selectivity for this interaction, even in a complex cellular environment, suggesting a reasonably strong mutual affinity.

In conclusion, it was demonstrated that the solvent exposed C-terminal α-helix of the GLUE protein scaffold can be dramatically modified and extended, so as to mimic the function of the gp41 C-peptide. ELISA and copurification data indicate that GLUE-Cpep selectively binds 5-helix, a protein that mimics the native C-peptide receptor. Unlike the isolated C-helix of enfuvirtide, GLUE-Cpep is soluble and well-folded in aqueous solution at room temperature (~25° C.) and is resistant to degradation in human serum at physiological temperature (~37° C.). Thus, this protein drug lead overcomes challenges faced by traditional peptide reagents and could represent a new reagent for inhibition of HIV entry. Additionally, helix-grafting onto PH and PH-like domains, such as GLUE, might be a general approach to the development of new reagents of interest to a diverse set of diseases that rely on helix-driven assembly. Finally, GLUE-Cpep serves as a starting point for the generation of higher affinity and more selective mutants through the application of high-throughput screening or selection methods. Such experiments are currently underway and will be reported in due course.

Methods for Example 1.

Protein Purification: Genes were cloned into pETDuet-1 using restriction enzymes BamHI and PacI, downstream of a His6× tag and transformed into BL21s (DE3). Cells were grown in 2.5 L LB cultures containing 50 μg/mL carbenicillin at 37° C. to OD600=0.5 and induced with 1 mM IPTG at 25° C. overnight. Cells were then collected by centrifugation, resuspended in Tris buffer (20 mM Tris pH 7.4, 100 mM NaCl, 10 mM $(NH_4)_2SO_4$) and stored at −20° C. Frozen pellets were thawed and sonicated with 1 second pulses for 2 minutes. The lysate was cleared by centrifugation (15,000 rpm 30 min.) and the supernatant was mixed with 1 mL of Ni-NTA agarose resin for 1 hour at 4° C. The resin was collected by centrifugation (4,750 rpm, 10 min.). The resin was sequentially washed with 50 mL of buffer containing 20 mM imidazole, 10 mL buffer containing 50 mM imidazole, and 5 mL buffer containing 100 mM imidazole. The protein was then eluted with 4 mL buffer containing 400 mM imidazole. The proteins were dialyzed against Tris buffer and analyzed for purity by SDS-PAGE shown below. Purified protein concentrations were quantified using Beer's Law at an absorbance of 280 nm, following standard practice (Grimsley, G. R.; Pace, C. N. Current Protocols in Protein Science (2003), 3.1.1-3.1.9). In general, GLUE-Cpep was expressed as a soluble protein (~3 mg/L of E. coli culture).

Resolublization from Inclusion Bodies: 5 Helix-His was cloned into a modified pETDuet-1 vector using restriction enzymes NdeI and KpnI and transformed into BL21s (DE3). Cells were induced to express 5 HelixHis6× and lysed as described above. The lysate was cleared by centrifugation (15,000 rpm, 30 min.) and the supernatant discarded. The pellet was washed twice with Tris buffer containing 0.5% Triton® X-100 and once with Tris buffer. The pellet was resuspended in urea buffer (Tris buffer with 8 M urea and 10 mM imidazole) to resolubilize the inclusion bodies and cleared by centrifugation (9,500 rpm, 30 min.) The supernatant was mixed with 1 mL of Ni-NTA agarose resin for 1 hour at 4° C. The resin was collected by centrifugation (4,750 rpm, 4 min.). The resin was washed with 50 mL of urea buffer and eluted with 40 mL of urea elution buffer (Tris buffer with 6 M urea and 100 mM imidazole) into 500 mL Tris buffer by gravity dripping while stirring to refold the protein. The 540 mL elution was run through a column containing 1 mL of Ni-NTA agarose resin and eluted with 5 mL Tris buffer containing 400 mM imidazole. The protein was then eluted with 4 mL buffer containing 400 mM imidazole. The proteins were dialyzed against buffer and analyzed for purity by SDS-PAGE and analyzed for refolding by CD. Purified proteins were quantified using Beer's Law at an absorbance of 280 nm.

Circular Dichroism: Proteins were purified as described above. Separately, each protein was diluted to 7-9 µM in Tris buffer (20 mM Tris pH 7.4, 100 mM NaCl, 10 mM $(NH_4)_2SO_4$). Wavelength data are the average of three scans from 250 nm to 200 nm in 1 nm steps at 25° C. Thermal denaturation experiments at 222 nm were run from 0 to 90° C. in two-degree steps at a two-degree/minute rate of increase with one-minute equilibration and data averaging at each temperature. Tm values were obtained from minima of the first derivative of θ versus 1/T plots.

Serum Stability Assay: Using a previously described assay for serum stability (Jenssen, H.; Aspmo, S. I. Methods Mol Biol 2008, 494, 177. 3 Blakeley, B. D), GLUE-Cpep was cloned into pET-28a(+) with an N-terminal FLAG tag (DDDDK) using restriction enzymes NdeI and HindIII. The completed construct was transformed into BL21s (DE3) and purified as described previously. 1 mL of RPMI supplemented with 25% (v/v) of human serum was equilibrated at 37° C. GLUE-Cpep was added to the solution to obtain a final concentration of 50 µg/mL and incubated at 37° C. At known time intervals of 0.5, 1, 2, 4, 8, or 12 hours, 100 µL of the reaction solution was removed and denatured at 94° C. for 20 minutes and stored at −80° C. Samples were separated by SDS-PAGE and transferred to a nitrocellulose membrane via an iBlot western blotting apparatus. The membrane was washed with PBS and incubated in LI-COR Blocking Buffer at 4° C. for 1 hour. The membrane was then incubated with a mouse anti-DDDDK antibody (antiFLAG) in LI-COR Blocking Buffer for 1 hour at 4° C. The membrane was washed 3× with PBS containing 0.1% Tween-20, and then incubated with a IRDye 800CW Goat anti-mouse IgG-LI-COR secondary antibody in LI-COR Blocking Buffer for 1 hour at room temperature. The membrane was washed 3× with PBS containing 0.1% Tween-20 and imaged using the Odyssey Classic Infrared Imager.

Split-Superpositive GFP (split-spGFP) Reassembly Assay: Split-spGFP reassembly experiments were performed as previously described (Chapman, A. M.; 3 McNaughton, B. R. Molecular BioSystems 2012, 8, 2036). N-terminal superpositive GFP tethered to the 5-helix was cloned into pETDuet-1 using restriction enzymes BamHI and PacI. The completed construct was transformed into BL21s (DE3) and the cells were made electrocompetent via standard protocols. Separately, GLUE-Cpep and C-peptide tethered to the C-terminal fragment of superpositive GFP were independently cloned into pBAD using restriction enzymes NcoI and BsrGI. Constructs were electroporated into electrocompetent BL21s (DE3) containing the N-terminal superpositive GFP plasmid, pulsing at 1.8 kV in a 1 mm cuvette. Cells were allowed to recover at 37° C. for 1 hour, and then plated onto agar plates containing carbenicillin and kanamycin. Individual colonies were picked and passaged once, followed by induction at 37° C. with 1 mM IPTG and 0.2% arabinosewhen cultures reached an OD600 of 0.5. After 6 hours, cells were spun down and resuspended in 5 mL PBS. GFP fluorescence was measured by MoFlo Flow Cytometer.

ELISA: Separately, wt-GLUE, GLUE-Cpep, and the C-peptide were cloned into MCS1 of pETDuet-1 with FLAG tags using restriction enzymes NcoI and NotI. The 5-helix with a C-terminal His6× tag was cloned into MCS2 of pETDuet-1 using restriction enzymes NdeI and KpnI. Completed constructs were transformed into BL21s (DE3). Cells containing the co-expressed pair were inoculated and induced as described previously. Cells were spun down and resuspended in lysis buffer (20 mM Hepes pH 7.5, 100 mM NaCl), lysed by sonication, and spun down to remove cell debris. Cleared lysates were incubated on clear Ni-NTA coated plates for 1 hour at room temperature and washed 4× with 200 µL wash buffer (20 mM Hepes pH 7.5, 150 mM NaCl, 0.05% Tween-20, 0.01 mg/mL BSA). HRP-conjugated mouse anti-DDDDK antibody in LiCor Blocking Buffer was incubated for 1 hour at room temperature, followed by 4×200 µL washes. Colorimetry was developed using TMB-One substrate and absorbance was measured at 655 nm on a SynergyMx Microplate Reader.

ELISA Binding Assay in Human Serum: GLUE-Cpep was cloned into pET-28a(+) with an N-terminal FLAG tag using restriction enzymes NdeI and HindIII. 5-helix was cloned into pETDuet-1 with an N-terminal AviTag and a C-terminal His6× tag using restriction enzymes NcoI and PacI. The completed constructs were transformed into BL21s (DE3) and purified as described previously. AviTag-5 helix was conjugated to biotin using Avidity BioMix protocols and purified BirA Protein Ligase at 1.0 mg/mL. Biotin conjugation was confirmed by Mass Spectometry (see FIG. 7). Separately, 5 mL of RPMI supplemented with 25% (v/v) human serum, 5 mL of boiled RPMI supplemented with 25% (v/v) of human serum, and 5 mL of (1×) PBS were equilibrated at 37° C. GLUE-Cpep was added to each solution to a final concentration of 50 nM, and incubated at 37° C. for 4 or 12 hours. 200 µL wash buffer (1×PBS pH 7.4, 0.1% Tween-20, 0.02 mg/mL BSA) was incubated on clear streptavidin coated plates for 1 hour at room temperature to block. 100 µL of Biotinylated 5-helix at a concentration of 10 µg/mL was incubated for 1 hour at room temperature and washed 4× with 200 µL wash buffer. 100 µL of human serumincubated GLUE-Cpep solutions were incubated on the plates for 1 hour at room temperature and washed 4× with 200 μL wash buffer. HRP-conjugated mouse anti-DDDDK antibody in LiCor blocking buffer was incubated for 1 hour at room temperature, followed by 5×200 μL washes. Colorimetry was developed using TMB-One substrate and absorbance was measured at 655 nm on a SynergyMx Microplate Reader. These ELISA data can be found in FIG. 8.

Lysate Ni-NTA Pulldown Assay: GLUE-Cpep was cloned into MCS1 of pETDuet-1 using restriction enzymes NcoI and NotI. The 5 helix with a C-terminal His6× tag was cloned into MCS2 of pETDuet-1 using the restriction enzymes NdeI and KpnI. Completed constructs were transformed into BL21s (DE3). Cells containing the co-expressed pair were inoculated and induced as described previously. Cells were spun down and resuspended in lysis buffer (100 mM NaCl, 20 mM Tris pH 7.4, 10 mM (NH4)2SO4), lysed by sonication, and spun down to remove cell debris. Cleared lysate was incubated with 200 μL Ni-NTA agarose resin for 1 hour. Ni-NTA agarose was washed with 8 mL lysis buffer and with 10 mM imidazole. Proteins were eluted with 500 μL lysis buffer containing 400 mM imidazole. The pulldown was analyzed by SDS-PAGE and confirmed by Mass Spectroscopy.

TABLE 1

Sequence used in Example 1.

| SEQ ID NO: | Sequence | Name | Use |
|---|---|---|---|
| 9 | MGSSHHHHHHSQDPEYWHYVETTSSGQPLLR EGEKDIFIDQSVGLYHGKSKILQRQRGRIFLTS QRIIYIDDAKPTQNSLGLELDDLAYVNYSSGFL TRSPALILFFKDPSSSTEFVQLSFRKSDGVLFSQ ATERALENILT | His6x-wtGLUE | For circular dichroism experiments |
| 10 | MQLLSGIVQQQNNLLRAIEAQQHLLQLTVWGI KQLQARILAGGSGGHTTWMEWDREINNYTSLI HSLIEESQNQQEKNEQELLEGSSGGQLLSGIVQ QQNNLLRAIEAQQHLLQLTVWGIKQLQARILA GGSGGHTTWMEWDREINNYTSLIHSLIEESQN QQEKNEQELLEGSSGGQLLSGIVQQQNNLLRA IEAQQHLLQLTVWGIKQLQARILAGGHHHHH | 5-Helix-His6x (Also used in ELISA experiment and lysate Ni-NTA pulldown assay experiments) | |
| 11 | MGSSHHHHHHSQDPGLNDIFEAQKIEWHEGG SGGSGGTEYWHYVETTSSGQPLLREGEKDIAI DQSVGLYHGKSKILQRQRGRIFLTSQRIIYIDD AKPTQNSLGLELDDLAYVNYSSGFLTRSPALIL FFKDPSSSTEFVQLSFRKSDGVWFSWATEIALY TILIHSLIEESQNQQEKNEQELL | His6x-GLUE-Cpep | |
| 12 | MDYKDDDDKGGSEYWHYVETTSSGQPLLRE GEKDIFIDQSVGLYHGKSKILQRQRGRIFLTSQ RIIYIDDAKPTQNSLGLELDDLAYVNYSSGFLT RSPALILFFKDPSSSTEFVQLSFRKSDGVLFSQA TERALENILT | FLAG-GLUE | For ELISA experiments |
| 13 | MDYKDDDDKGGSEYWHYVETTSSGQPLLRE GEKDIAIDQSVGLYHGKSKILQRQRGRIFLTSQ RIIYIDDAKPTQNSLGLELDDLAYVNYSSGFLT RSPALILFFKDPSSSTEFVQLSFRKSDGVWFSW ATEIALYTILIHSLIEESQNQQEKNEQELL | FLAG-GLUE-Cpep | |
| 14 | MDYKDDDDKGGSWMEWDREINNYTSLIHSLI EESQNQQEKNEQELL | FLAG-CHR | |
| 15 | MGSSHHHHHHSSGLVPRGSHMDYKDDDDKG GSEYWHYVETTSSGQPLLREGEKDIAIDQSVG LYHGKSKILQRQRGRIFLTSQRIIYIDDAKPTQN SLGLELDDLAYVNYSSGFLTRSPALILFFKDPS SSTEFVQLSFRKSDGVWFSWATEIALYTILIHS LIEESQNQQEKNEQELL | FLAG-GLUE-Cpep | For serum stability experiments |
| 16 | MEYWHYVETTSSGQPLLREGEKDIAIDQSVGL YHGKSKILQRQRGRIFLTSQRIIYIDDAKPTQNS LGLELDDLAYVNYSSGFLTRSPALILFFKDPSS STEFVQLSFRKSDGVWFSWATEIALYTILIHSLI EESQNQQEKNEQELLGGSGGSGTSGGSGKNGI KAKFKIRHNVKDGSVQLADHYQQNTPIGRGP VLLPRNHYLSTRSKLSKPKEKRDHMVLLEFV TAAGIKHGRDERYK | GLUE-Cpep-CscGFP | For split-superpositive GFP reassembly assay experiments |
| 17 | MGWMEWDREINNYTSLIHSLIEESQNQQEKNE QELLGGSGGSGTSGGSGKNGIKAKFKIRHNVK DGSVQLADHYQQNTPIGRGPVLLPRNHYLSTR SKLSKDPKEKRDHMVLLEFVTAAGIKHGRDE RYK | C-peptide-CscGFP | |

TABLE 1-continued

Sequence used in Example 1.

| SEQ ID NO: | Sequence | Name | Use |
|---|---|---|---|
| 18 | MGHHHHHHGGASKGERLFRGKVPILVELKGD VNGHKFSVRGEGKGDATRGKLTLKFICTTGKL PVPWPTLVTTLTYGVQCFSRYPKHMKRHDFF KSAMPKGYVQERTISFKKDGKYKTRAEVKFE GRTLVNRIKLKGRDFKEKGNILGHKLRYNFNS HKVYITADKRGGSGSGSSGGTQLLSGIVQQQN NLLRAIEAQQHLLQLTVWGIKQLQARILAGGS GGHTTWMEWDREINNYTSLIHSLIEESQNQQE KNEQELLEGSSGGQLLSGIVQQQNNLLRAIEA QQHLLQLTVWGIKQLQARILAGGSGGHTTWM EWDREINNYTSLIHSLIEESQNQQEKNEQELLE GSSGGQLLSGIVQQQNNLLRAIEAQQHLLQLT VWGIKQLQARILAGGHHHHHH | NscGFP-5helix | |
| 19 | MEYWHYVETTSSGQPLLREGEKDIAIDQSVGL YHGKSKILQRQRGRFLTSQRIIYIDDAKPTQNS LGLELDDLAYVNYSSGFLTRSPALILFFKDPSS STEFVQLSFRKSDGVWFSWATEIALYTILIHSLI EESQNQQEKNEQELL | GLUE-Cpep | For lysate Ni-NTA pulldown assay experiments |

Example 2

Proteins as Therapeutics: An Alternative to Small Molecule Drug Design

Historically, the majority of therapeutic agents have been small organic molecules (<800 Da). This is due to small molecules' ability to successfully modulate cell fate by targeting well-defined hydrophobic pockets on proteins. While effective, this strategy is limited to the ~20% of the proteome that was naturally evolved to bind metabolites.[1] This restraint significantly affects the number of molecular targets and corresponding therapeutics. In fact, ~50% of current prescription drugs target just three gene families: G-protein-coupled receptors, nuclear receptors, and ion channels. A large part of the proteome remains untouched and lies beyond the reach of small molecules.

Protein-protein interactions (PPIs) are important for mediating cell function. Probing these interactions is of significant interest because it could lead to pharmaceutical development and a more in depth understanding of system biology Certain characteristics of PPIs make it difficult for small molecules to target them. The first, and possibly largest reason for this challenge is the size of PPIs. PPIs can create surfaces spanning ~1500 to 3000 Å that are filled with polar and hydrophobic interactions that can make it difficult for a small molecule to perturb. Some PPIs are commonly thought of as featureless since there in no binding cleft for small molecules. If a small molecule were to bind in a featureless region, only one face or side of the molecule would be able to interact with that protein interface. In some cases it would be optimal to have something larger (>800 Da) that could form multiple contacts with the flat surface in order to disturb these PPIs.

Recent advancements in the development of biopharmaceuticals (also referred to as biologics: nucleic acids, peptides, and proteins) has led to a large increase in the number of FDA approved protein therapeutics. Proteins offer a promising alternative to small molecules for a variety of reasons, the foremost being their size, functional diversity and high folding energies. With advancing technologies in molecular biology, like recombinant protein expression, purification, and phage display it is likely that proteins will continue to be developed towards accessing new parts of the proteome. While small molecules will always play a pivotal role in drug therapy, proteins and other biologics can take on functions for disturbing previously "undruggable" protein-protein targets.

Example 3

Mechanism of Membrane Fusion in Enveloped Virus HIV-1

HIV-1 is a notorious human pathogen that affects ~35 million people worldwide. HIV-1 is considered an enveloped virus because its nucelocapsid, which contains the viral genome, is surround by a lipid membrane. Membrane fusion of HIV-1 is mediated by the glycoprotein, gp160. gp160 is cleaved by a protease into two noncovalently bonded glycoproteins; gp120 and gp41. gp120, the surface subunit, is essential for recognizing the target cell's surface receptor. gp41, the transmembrane subunit, contains several regions that are responsible for the merge of the viral membrane and the target cell membrane (FIG. 9A). The fusion peptide, FP, is important for inducing viral entry, promoted by anchoring itself into the host membrane. X-ray crystallography shows that the C- and N-terminal heptad repeats (CHR and NHR) exist as a trimer of hairpins, in one of its final fusion conformations. NHR is able to self interact forming a central trimeric coiled-coil with three large hydrophobic pockets. The three helical CHR peptides (shown in pink) are able to bind NHR (shown in purple) in an antiparallel fashion (FIG. 9B). This formation, referred to as the 6-helix bundle (6HB), is key for successful infection.

HIV-1 viral entry begins with gp120 recognition of a CD4 receptor and attachment to a co-receptor (CCR5 or CXCR4). This event triggers conformational rearrangements that lead to shedding of gp120 and subsequent unveiling of the FP from gp41. The FP then inserts itself into the host cell membrane, forming a thermodynamically stable extended pre-hairpin intermediate. Conformational changes in the cell membrane lead to the intermediate's eventual collapse and formation of the 6HB, bringing the two membranes closer together. Energy released by establishment of the 6HB allows for the creation of the fusion pore and eventual viral entry. FIG. 10 depicts the key intermediates in this process. Kinetic studies have shown the extended pre-hairpin intermediate lasts for minutes, making it an excellent therapeutic target. Potential inhibitors could bind the hydrophobic grooves of the NHR trimer, and impede CHR from binding NHR to form the 6HB.

Example 4

Previous Efforts in Targeting Membrane Fusion

α-Helical peptides mimicking NHR and CHR of gp41 are a validated therapeutic approach for membrane fusion. NHR peptides are able to inhibit infection with micromolar concentrations but often aggregate because of their hydrophobic residues. CHR peptides (also referred to as C-peptides) have proven to be more potent and effective than NHR peptides. For example, C34 (residues 628-661 of CHR) is effective at inhibiting HIV-1 viral membrane fusion in nanomolar concentrations. T-20, marketed as Fuzeon by Roche, is currently the only FDA approved peptide therapeutic for HIV-1. Its sequence begins with residues from the C-terminus of CHR through the residues of the Membrane Proximal Region (MPER, residues 638-673). T-20 is a classic example of the use of peptides therapeutics, by being the first entry inhibitor in a class of anti HIV-1 drugs.

Despite their success, α-helical peptides still have considerable drawbacks, namely cost of production and sensitivity to degradation. Patients diagnosed with HIV-1 are often given T-20 as a last resort. Treatment with T-20 costs ~$20,000 per year and requires heavy dosage because of its rapid depletion from the body. Proteolytic stability is a common issue for α-helical peptides because they are often found disordered in solution, which makes them susceptible to degradation. In order for a peptide to bind its desired target a large entropic cost is required to go from its partially unfolded state to an ordered conformation. Peptide therapeutics have sought to overcome the limitations of helical peptides by methods of stabilization and structured mimics. Helix stabilization constrains the peptide so it can no longer move freely. Common methods for this are forming salt bridges, chelation with metals, hydrocarbon stapling and covalent cyclization. Helical mimics imitate the topography of the peptide, allowing for correct orientations of the functional groups. Approaches for this includes using α/β peptides, terphenyls, and peptoids. These methods have shortcomings of their own and can result in a decrease of the original peptide's potency. Increased optimization is still of significant interest despite the development of new strategies for cost effective and efficient peptide synthesis.

Example 5

Helix Grafted Display: A New Method for Helix Stabilization

Protein grafting could be an ideal method for helix stabilization due to the large success with N- and C-peptides as HIV-1 gp41-1 binders. Protein grafting is used to transfer the biological function of a ligand onto the surface of another protein. Kim and co-workers applied this method with the C-peptide of HIV-1, grafting it onto a GCN4 leucine zipper. Their protein, C34-GCN4, showed similar activity to the native C-peptide. However, helix stabilization is still a challenge when grafting onto a pre-established helical interface. It was hypothesized a protein with a solvent exposed helix could be stabilized by its tertiary structure and would be better suited for grafting. The tertiary structure was predicted to promote helix stabilization, thus overcoming proteolytic degradation and the entropic costs of binding.

Pleckstrin Homology (PH) domains have a C-terminal solvent exposed helix that fits in a cleft formed by the surrounding β-sheets. These domains are generally found in proteins involved in cell trafficking and function in binding phosphoinositides. These proteins are ~120 residues which makes for quick insertion into a bacterial vector. The native function of PH domains can also be turned off by a single mutation via site directed mutagenesis. The hydrophobic effect suggests that the buried residues are critical for providing the protein's tertiary structure. If those residues were untouched and only solvent exposed helical residues mutated, the interface could be altered to match the binding face of the peptide. FIG. 2 depicts the helix grafted display method developed herein (Example 1). These findings support helix-grafted display proteins as an excellent platform for potent and selective binder of HIV-1 gp41.

Example 6

Expanding Helix Grafted Display onto Other PH and PH-Like Domains

GLUE-Cpep was a first generation model of helical ligand display. This method could be expanded to show its flexibility by grafting onto other PH domains. There are a variety of other PH domains that have been well characterized in the Protein Databank. The scaffolds selected for characterization are known to be expressible in *E. coli*, have varying helical content, and are endogenous to humans or mammals (Table 2, FIG. 11). DOK5 was an interesting candidate because it had a high percentage helicity, found by dividing the number of helical residues by total residues, and had the smallest number of total residues. To determine if helix length was a factor for grafting, a PH domain with a short helix was found; Dynamin had the shortest number of helix residues at 13. Disulfide bonds are able to help stabilize a protein's tertiary structure. Two PH domains with this characteristic and varying helix lengths were thus sought-after. The search turned up with AKT2 and PKB, which have 20 and 30 helical C-terminal residues, respectively. HOMER was the only nonhuman scaffold analyzed (endogenous to Norway rats) and was midsized in helical content (in comparison to selected scaffolds). Two PTB domains were also tested, ELMO and APPL1. Phosphotyrosine-binding (PTB) domains are very similar to PH domains, but contain an extra α-helix in their structure. APPL1 PTB contains a C-terminal helix and a second helix in the middle of its structure. ELMO on the other hand, contains a helix on both the N- and C-terminus. The PTB domain of APPL1 has the longest helix at 36 residues; this protein also has a PH domain. Both the PTB and PH domain were selected as a potential scaffold so their expression could be compared.

TABLE 2

Candidate PH and PH like domains

| | | # residues | | % helix | | |
|---|---|---|---|---|---|---|
| Domains | Pdb | Helix | Total | residues | Human | disulfide |
| GLUE | 2cay | 18 | 128 | 14 | No | No |
| HOMER | 1I2H | 26 | 116 | 22 | No | No |

TABLE 2-continued

Candidate PH and PH like domains

| | | # residues | | % helix | | |
|---|---|---|---|---|---|---|
| Domains | Pdb | Helix | Total | residues | Human | disulfide |
| PLECKSTRIN | 2I5F | 17 | 105 | 16 | Yes | No |
| PKB | 1UNP | 30 | 119 | 25 | Yes | Yes |
| AKT2 | 1P6S | 20 | 111 | 18 | Yes | Yes |
| DYNAMIN | 2DYN | 13 | 105 | 12 | Yes | No |
| APPL1-PTB | 2ELA | 36 | 145 | 25 | Yes | No |
| APPL1-PH | 2ELB | 18 | 112 | 16 | Yes | No |
| DOK5 | 1J0W | 21 | 104 | 20 | Yes | No |
| ELMO (N-term) | 2VSZ | 27 | 147 | 19 | Yes | No |
| ELMO (C-term) | 2VSZ | 18 | 147 | 12 | Yes | No |

All proteins were produced recombinantly in a pET vector with a His$_{6x}$ tag. The nine selected PH domains were then transformed in E. coli, grown up under the same conditions and purified identically. Their expression was quantified in mg/L and compared to wtGLUE (FIG. 12A). The solubility of each protein was also visualized on an SDS page gel (FIG. 12B and FIG. 12C). If something was poorly soluble in comparison to wtGLUE it was eliminated. APPL1 PTB and APPL1 PH showed minimal expression when ran on a protein gel, whereas PKB and Dynamin could not be visualized. The amount of purified protein for these scaffolds was also minimal so they were subsequently eliminated. Despite DOK5 expressing at ~2 mg/L, it moved forward since it looked very soluble according to the protein gel.

HOMER, PLECKSTRIN, ELMO, AKT2, and DOK5, were then grafted onto following the same helix display method. Each scaffold had varying helical lengths, but only helical residues that were not crucial for the protein's structure (i.e. solvent exposed) were mutated to mimic the binding face of the C-peptide. In some cases, the helices extended beyond the β-sheet formation and were truncated. Since ELMO had two terminal helices, it was grafted onto both ends (FIG. 13). The grafting technique for the N-terminal helix was slightly different since most of its helix is solvent exposed. The helix was reduced and the C-peptide sequence replaced it. Not knowing how much could be grafted onto the N-terminal end, a shortened version called C26-ELMO was made. Even though this caused a loss of eight C-terminal residues of CHR, the sequence still included the WWI motif, important for interacting with the 5-Helix. Each grafted scaffolds was then characterized by the same procedure as their wild-type (FIG. 14).

HOMER-C34, ELMO-C34, C26-ELMO expressed the best. Interestingly, C26-ELMO and ELMO-C34 expressed even better than wtELMO. HOMER-Cpep, despite its comparable expression to GLUE-Cpep was eliminated since it was not endogenous to humans. Moving forward ELMO was the focus of the efforts since it expressed well and was human derived (minimizing potential immunogenicity).

Example 7

Characterization of C26-ELMO and ELMO-C34

CD was used to verify that the grafting technique did not greatly alter the protein's secondary structure, but rather enhanced its helicity (just as previously done with GLUE). In FIG. 15A, the wavelength scans for C26-ELMO and wtELMO are compared. Both showed α-helical characteristics and C26-ELMO demonstrated a stronger signal, indicative of improved helicity. ELMO-C34 will be characterized similarly in the upcoming future. Having confirmed the structural integrity of C26-ELMO, its binding interactions along with ELMO-C34 were investigated using the same techniques performed for GLUE-Cpep (FIG. 15B and FIG. 15C). C26-ELMO and ELMO-C34 had ELISA signals comparable to the positive control C34 and could also be purified alongside 5-Helix-$His_{6\times}$.

Example 8

Optimization of ELMO for Selective Inhibition of HIV-1

Unexpectedly, the wild-type form of ELMO (wtELMO) had a strong ELISA signal, suggesting wtELMO had some affinity for the 5-Helix bundle. This signal could be attributed to the native N-terminal helix positioning itself into the hydrophobic groove of the 5-Helix pocket. To corroborate this idea, the N-terminal helix of wtELMO was cut off (−N Helix ELMO and −N Helix KQQR ELMO) at two different positions to see if this would abolish binding to the 5-Helix model. The ELISA data showed both −N Helix ELMO constructs had significant decrease in signal. This data will be discussed vide infra. Moving forward, both the N- and C-terminal grafts were extended to possibly make a more potent binder and to test the flexibility of the graft. The natural N-terminal helix was herein truncated on all C-terminal ELMO grafts to ensure the binding of the grafted helix to the 5-Helix bundle.

As mentioned before, T-20 is a FDA approved peptide drug for inhibiting viral entry of HIV-1. Extending the previous C26-ELMO and ELMO-34 to include residues found in T-20 (the MPER region) could show the scaffolds malleability. In addition, grafting solely T-20 onto ELMO could make a more potent inhibitor and show the versatility of the helix grafted display method. The new N-terminal grafted scaffolds were named C34-ELMO, C46-ELMO, and T20-ELMO. C34-ELMO includes all 34 residues of the C peptide, C46-ELMO contains all the residues of C34 and extends through to T-20, and T20-ELMO only contains the residues of the marketed peptide drug. The C-terminal ELMO proteins were similarly altered, along with the above mentioned N terminal helix truncation to give −N helix ELMO-C34, −N Helix ELMO-C46, and −N Helix ELMO-T20.

Each new ELMO protein was expressed and binding interactions characterized, as previously done. From the gel in FIG. 16B it can be seen that cutting off the N terminal helix caused an increase in the solubility of ELMO. The gel also shows that alterations to the grafted helix caused a decrease in expression. Despite this decrease, each protein can be purified for further characterization. The new ELMO grafts showed less affinity for the 5-Helix bundle by ELISA and co-purification (FIG. 17). Perhaps because the C-terminal T-20 is thought to anchor itself into the membrane. The ELISA and co-purification data show comparable binding for C26-ELMO and C34-ELMO towards the 5-Helix bundle. Surprisingly, the N-terminal helix truncation had a large signal change between −N Helix ELMO-C34 and ELMO-C34 as shown by the ELISA data. The co-purification still showed a band, all be it small, −N helix ELMO-C34, suggesting some ability to bind the 5-Helix.

Example 9

In Cellulo HIV-1 Infection Assay

Despite some of their low affinity for the 5-Helix, it was still hypothesized the new ELMO grafts could inhibit HIV-1 infection. The ELMO grafts were tested as potential inhibitors of HIV-1 in cellulo. The validated assay uses a Lymphoblastoid CD4+ T-cell line with stably integrated EGFP (CEM-GFP) under the control of the HIV-1 long terminal repeat (LTR) promoter. 293T cells are simultaneously transfected with HIV-1 IIIB virus. The infected cells and non-infected cells are mixed together along with the desired inhibitor. If infection succeeds the number of infected GFP+ cells increases, which can be measured by flow cytometry (FIG. 18). The inhibition of each ELMO construct was determined in a dose depended manner and compared to C34 and T20 (FIG. 19). These data shows that wtELMO has no inhibitory effect on HIV-1, even with its N-terminal helix. The N-terminal grafts were more potent than their corresponding C-terminal graft (C34-ELMO in comparison to –N Helix ELMO-C34). The grafted constructs followed the same trends as shown by ELISA and co-purification, supporting characterization of potential viral entry inhibitors by using the 5-Helix Model. Most excitingly, C26 and C34 ELMO show some inhibition of infection at 250 nM. [Manuscript in preparation]. Affinity maturation on these grafted proteins could provide higher affinity variants that will hopefully have competitive inhibition constants with T20 and C34 and will be further investigated. Surprisingly, the T20 grafts showed similar inhibition to wtELMO. T20-ELMO may not be a potent inhibitor because the final four residues of T20 are attached to ELMO, which impede it from entering the membrane. The –N Helix ELMO C-34 (C-terminal T20 graft) could have lost potency because of the alterations made to the native T20 sequence due to the grafting method. T20 has already been characterized and optimized, so its possible modifications to its sequence could decrease potency. One of the unaltered residues on the C-terminal helix of ELMO contains a tryptophan. This tryptophan could potentially cause –N Helix ELMO-T20 to bind in a manner that cannot outcompete formation of the 6HB. Further grafts of ELMO would be necessary to confirm these postulations.

Optimization of helix-grafted display will be the continued focus of research. C-peptide will be grafted onto alternative scaffolds, in the hopes of finding additional potent inhibitors of HIV-1. Since the mechanism of membrane fusion is similar for enveloped viruses, helix-grafted display could be applied to their corresponding α-helical proteins to find potent inhibitors. Attaching other viral C-peptides to these PH domains could have varying solubility. PLECKSTRIN, HOMER, ELMO, AKT2, DOK5 would be excellent potential scaffolds since they express well as their wild-type. Further investigations could show which PH domains are the most malleable to grafting. Given these strong initial results, the helix-grafted display method shows promise as a platform for helix stabilization.

What is claimed is:

1. A method of producing a helix grafted protein, the method comprising:
   a. aligning the structure of a solvent exposed α-helix on a protein selected from the group consisting of GLUE and ELMO with the structure of all or a portion of a C-peptide from a virus, wherein the C-peptide comprises at least 10 amino acids;
   b. selecting 1-20 solvent exposed amino acid positions on the solvent exposed α-helix to install residues from the C-peptide sequence in such a way as to preserve the three-dimensional conformation of the residues from the C-peptide;

c. installing the selected residues on the solvent exposed α-helix to generate the grafted helix; and d. extending the grafted helix by attaching C-peptide residues to the terminus of the grafted helix, thereby producing the helix grafted protein.

2. The method of claim 1, wherein the protein is ELMO.

3. The method of claim 1, wherein the C-peptide comprises all or a portion of a gp41 C-peptide.

4. The method of claim 3, wherein the gp41 C-peptide comprises at least 10 residues of SEQ ID NO:2 (WMEWDREINNYTSLIHSLIEESQNQQEKNEQELL).

5. The method of claim 1, wherein the protein is GLUE and the sequence of the extended grafted helix comprises SEQ ID NO:3 (GVWFSWATEIALYTILIHSLIEESQNQQEKNEQELL).

6. The method of claim 1, wherein the protein is ELMO and the sequence of the extended grafted helix comprises SEQ ID NO:7 (WMEWDREINNYTSLIHSLIEESQNQQKQQRLNRLVE).

7. The method of claim 1, wherein the protein is ELMO and the sequence of the extended grafted helix comprises SEQ ID NO:8 (DKWEYWIWTIGLYTLLGKSLIEESQNQQEKNEQELL).

8. The method of claim 1, wherein the protein is ELMO and wherein the helix of ELMO is truncated.

9. The method of claim 1, wherein the protein is ELMO and the C-peptide comprises residues 116 to 161 of SEQ ID NO:4.

10. The method of claim 1, wherein the protein is ELMO and the sequence of the extended grafted helix comprises SEQ ID NO:8 (DKWEYWIWTIGLYTLLGKSLIEESQNQQEKNEQELL) and residues 150 to 161 of SEQ ID NO:4.

* * * * *